US008663931B2

(12) United States Patent
Saito et al.

(10) Patent No.: US 8,663,931 B2
(45) Date of Patent: Mar. 4, 2014

(54) METHOD FOR DETECTING RENAL DISEASE COMPRISING MEASURING HUMAN MEGALIN IN URINE

(75) Inventors: Akihiko Saito, Niigata (JP); Yasuhiko Tomino, Bunkyo-ku (JP); Katsuhiko Asanuma, Bunkyo-ku (JP); Shinya Ogasawara, Gosen (JP); Hiroyuki Kurosawa, Gosen (JP); Yoshiaki Hirayama, Gosen (JP)

(73) Assignees: Niigata University, Niigata (JP); Juntendo Educational Foundation, Tokyo (JP); Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/266,411

(22) PCT Filed: Apr. 27, 2010

(86) PCT No.: PCT/JP2010/057465
§ 371 (c)(1),
(2), (4) Date: Oct. 26, 2011

(87) PCT Pub. No.: WO2010/126043
PCT Pub. Date: Nov. 4, 2010

(65) Prior Publication Data
US 2012/0040374 A1    Feb. 16, 2012

(30) Foreign Application Priority Data

Apr. 27, 2009   (JP) ................................ 2009-108498

(51) Int. Cl.
*G01N 33/53*   (2006.01)
(52) U.S. Cl.
USPC ........................................... 435/7.1; 435/7.2
(58) Field of Classification Search
None
See application file for complete search history.

(56) References Cited

U.S. PATENT DOCUMENTS

| 7,955,809 B2 * | 6/2011 | Ogasawara et al. ............ 435/7.1 |
| 2004/0204357 A1 | 10/2004 | Brautigam et al. |
| 2004/0235161 A1 | 11/2004 | Tabata et al. |
| 2009/0117594 A1 | 5/2009 | Ogasawara et al. |
| 2010/0233738 A1 | 9/2010 | Hara et al. |

FOREIGN PATENT DOCUMENTS

| EP | 2 006 683 A1 | 12/2008 |
| EP | 2 426 495 A1 | 3/2012 |
| JP | 04-351962 | 12/1992 |
| JP | 08-105889 | 4/1996 |
| JP | 2005-528615 A | 9/2005 |
| JP | 2007-263750 A | 10/2007 |
| JP | 2007-536260 A | 12/2007 |
| JP | 2009-511913 A | 3/2009 |
| WO | WO-03/102493 A1 | 12/2003 |
| WO | WO-03/102593 A1 | 12/2003 |
| WO | WO-2005/107793 A2 | 11/2005 |
| WO | WO-2007/047458 A2 | 4/2007 |
| WO | WO-2009/041577 A1 | 4/2009 |

OTHER PUBLICATIONS

Norden et al. (J. Am. Soc. Nephrol. 2002 vol. 13, p. 125-133).*
Kuusniemi et al. Kidney International 2005 vol. 68, p. 121-132.*
Akihiko Saito et al., "Megalin, a Multiligand Endocytotic Receptor: The Role in the Development of Diabetic Nepropathy, Metabolic Syndrome-related Nephropathy and Uremia", Niigata Medical Journal, 2005, vol. 119, No. 1, pp. 1-9.
Hajime Yamazaki et al., "All Four Putative Ligand-Binding Domains in Megalin Contain Pathogenic Epitopes Capable of Inducing Passive Heymann Nephritis", J. Am. Soc. Nephrol., 1998, vol. 9, 1638-1644.
International Search Report PCT/JP2010/057465 dated Aug. 3, 2010.
De Jong, M. et al., "Megalin Is Essential for Renal Proximal Tubule Reabsorption of 111In-DTPA-Octreotide", The Journal of Nuclear Medicine, vol. 46, No. 10, Oct. 2005, pp. 1696-1700.
Final Office Action in U.S. Appl. No. 13/093,984 dated Aug. 6, 2013.
Final Office Action U.S. Appl. No. 12/293,992 dated Aug. 19, 2010.
Gburek et al., "Renal uptake of myoglobin is mediated by the endocytic receptors megalin and cubilin", Am J Physiol Renal Physiol 285: F451-F458, 2003.
http://www.abcam.com/index.html?t=115434&pt=1downloaded Mar. 21, 2011.
http://www.biognosisltd.co.uk/Exocell/Urinary%20Assays.htmldownloaded Mar. 21, 2011.
Ilse Raats et al., "Reduction in Glomerular Heparan Sulfate Correlates with Complement Deposition and Albuminuria in Active Heymann Nephritis", J. Am. Soc. Nephrol. 10: 1689-1699, 1999.
International Search Report in PCT/JP2007/056660 dated May 15, 2007.
International Search Report PCT/JP2010/057490 dated Jun. 8, 2010.
Jordan (The Protein Protocol Handbook, second edition, edited by Walker, year 2000, p. 1083-1088).
Knox M.D. et al., HIV and community. Mental Healthcare. The Johns Hopkins University Press Ltd., London, 1998, p. 25.
Kobayashi et al., "Conditions for Solubilization of Tamm-Horsfall Protein/Uromodulin in Human Urine and Establishment of a Sensitive and Accurate Enzyme-Linked Immunosorbent Assay (ELISA) Method", Archives of Biochemistry and Biophysics, vol. 388, No. 1, Apr. 1, 2001, pp. 113-120.
Kuusniemi et al., "Kidneys with heavy proteinuria show fibrosis, inflammation, and oxidative stress, but no tubular phenotypic change", Kidney International, vol. 68, (2005) pp. 121-132.

(Continued)

*Primary Examiner* — Jacob Cheu
(74) *Attorney, Agent, or Firm* — Foley & Lardner LLP

(57) ABSTRACT

This invention provides a diagnostic kit and a diagnostic marker used for diagnosing a renal disease. This invention also provides a method for detecting a renal disease comprising measuring at least one type of human megalin existing in urine selected from among full-length human megalin and human megalin fragments of (i) to (iii): (i) full-length human megalin; (ii) a human megalin endodomain fragment lacking a human megalin ectodomain; and (iii) a human megalin ectodomain fragment lacking a human megalin endodomain.

4 Claims, 21 Drawing Sheets

(56) References Cited

OTHER PUBLICATIONS

Non-Final Office Action U.S. Appl. No. 12/293,992 dated Dec. 15, 2009.
Non-Final Office Action U.S. Appl. No. 12/293,992 dated Sep. 28, 2009.
Non-final office action U.S. Appl. No. 13/093,984 dated Jan. 12, 2012.
Notice of Allowance U.S. Appl. No. 12/293,992 dated Feb. 8, 2011.
Office Action in JP Appln No: 2009-108498 dated Jul. 30, 2013.
Office Action in U.S. Appl. No. 13/266,397 dated Janaury 22, 2013.
Russian Office Action Application No. 2008142534/15 (055325) w/English translation.
Saito et al., "Megalin, a Multiligand Endocytotic Receptor: The Role in the Development of Diabetic Nephropathy, Metabolic Syndrome—related Nephropathy and Uremia", Niigata Medical Journal, 119(1), Jan. 10, 2005, pp. 1-5.
Search Report in EP Appln No: 10769753.4, dated February 11, 2013.
Supplementary Search Report in EP 07 74 0098 dated Aug. 24, 2009.
Thrailkill, K.M. et al., "Microalbuminuria in Type 1 Diabetes Is Associated Wuth Enhanced Excretion of the Endocytic Multilignad Receptors Megalin and Cubilin", Diabetes Care, Vol. 32, No. 7, Apr. 14, 2009, p. 1266-1268.

Van Venrooij, W.J. et al., Manual of Biological Markers of Disease, Kluwer Academic Publishers, The Netherlands, 1993, vol. 1, AMAN-C1.1/5.
Willnow et al. (PNAS 1996 vol. 93 p. 8460-8464).
EP Application No. 10769753.4, Search Report Dated February 11, 2013.
Norden, A G W et al., "Urinary Megalin Deficiency Inplicates Abnormal Tubular Endocytic Function in Fanconi Syndrome", Journal of the American Society of Nephrology, Williams and Wilkins, Baltimore, MD, US, vol. 13, Jan. 1, 2002, p. 125-133.
Ogasawara, Shinya et al., "Significance of Urinary Full-Legnth and Ectodomain Forms of Megalin in Patients With Type 2 Diabetes.", Diabetes Care May 2012 Lnkd-pubmed: 22410816, vol. 35, No. 5, May 2012, p. 1112-1118.
Thrailkill, K.M. et al., "Microalbuminuria in Type 1 Diabetes Is Associated With Enhanced Excretion of the Endocytic Multiligand Receptors Megalin and Cubilin", Diabetes Care, vol. 32, No. 7, Apr. 14, 2009, p. 1266-1268.
Wilmer, Martijn et al., "Urinary Protein Excretion Pattern and Renal Expression of Megalin and Cubilin in Nephropathic Cystinosis.", American Journal of Kidney Diseases, vol. 51, Jan. 1, 2008, pp. 893-903.
EP Application No. 10769741.9, Search Report Dated Jan. 9, 2013.

\* cited by examiner

METHOD FOR DETECTING RENAL DISEASE COMPRISING MEASURING HUMAN MEGALIN IN URINE

CROSS-REFERENCE TO RELATED APPLICATIONS

This application is the U.S. national phase of PCT/JP2010/057465, filed Apr. 27, 2010, which claims priority from Japanese patent application No. 2009-108498, filed Apr. 27, 2009. The entire subject matter of each of these applications is incorporated by reference.

TECHNICAL FIELD

The present invention relates to a detection kit and a detection marker used for diagnosing a renal disease. Also, the present invention relates to a method for diagnosing a renal disease using the megalin level in urine as an indicator for diagnosing a renal disorder in the form of a marker. In addition, the present invention relates to a method for evaluating effects of treating a renal disease.

BACKGROUND OF THE INVENTION

Megalin is also known as the glycoprotein 330 (gp330) or low-density lipoprotein (LDL)-receptor related protein 2 (LRP2). It is a glycoprotein expressed in the renal proximal tubular epithelial cells with a molecular weight of approximately 600 kDa (Non-Patent Documents 1 and 2).

Megalin serves as an endocytic receptor associated with endocytosis/resorption of a protein or the like in the proximal tubular lumen in the kidney before urinary excretion. A ligand of a resorbed protein or the like is then degraded by a lysosome in the proximal tubular epithelial cells (Non-Patent Document 3).

In recent years, Flavia, F. J. et al. reported, as results attained by a cell culture experiment using renal proximal tubular epithelial cells, that two types of megalins exist (i.e., full-length membrane-bound megalin and soluble megalin lacking an endodomain (a fragment containing an ectodomain)) (Non-Patent Document 4).

In addition, it has been reported that such soluble megalin (i.e., a fragment containing an ectodomain but lacking an endodomain) is constituted by a notch-like cleavage mechanism, which is mediated by the first-phase cleavage of an ectodomain in the vicinity of a cell membrane with metalloprotease and the subsequent second-phase cleavage of a transmembrane domain located inside the membrane with γ-serectase (Non-Patent Documents 5, 6, 7, and 8).

Many cell transmembrane glycoproteins have heretofore been known in which ectodomains are released from the cells to the periphery (i.e., shedding). It has been found in recent years that shedding takes place upon cleavage of a membrane protein by a given protease triggered by intracellular and extracellular signals. In addition, it has been found that such cleavage takes place in a cell transmembrane domain or endodomain in a chained manner and the cleaved fragment also functions as a signal molecule inside and outside the cell. The same applies to the megalin cleavage mechanism, and such cleavage mechanism plays a role in regulation of proximal tubular epithelial cell functions starting from the formation of a signal functional molecule (Non-Patent Documents 6 and 7). Two types of enzymes play a role in such cleavage procedures, and they are collectively referred to as metalloprotease and serectase. It has been found that activity thereof is associated with regulation of functions of various membrane proteins and is very important for diseases such as cancer or Alzheimer's disease, as well as for basic physiological functions such as cell differentiation and growth. Examples of membrane proteins in which ectodomain-shedding has been observed include tyrosine kinase growth factor receptors represented by the EGF receptor (EGFR) family, various interleukin (IL) receptors, adhesion molecules, and LDL receptors (LRP). As described above, megalin is a transmembrane glycoprotein of the LDL receptor superfamily and has been known to experience ectodomain-shedding as reported in Non-Patent Documents 5, 6, 7, and 8.

In addition, a method for measuring the amount of megalin excreted into the urine had been reported (Patent Document 1). However, patterns of human megalin, which had been subjected to cleavage modification, such as shedding by a protease in vivo, excreted into the urine have not yet been evaluated.

PRIOR ART DOCUMENTS

Patent Document

Patent Document: 1: WO 2007/119563

Non-Patent Documents

Non-Patent Document 1: Christensen, E. I., Willnow, T. E., 1999, J. Am. Soc. Nephrol. 10, 2224-2236
Non-Patent Document 2: Zheng, G., McCluskey, R. T. et al., 1994, J. Histochem. Cytochem. 42, 531-542
Non-Patent Document 3: Mausbach, A. B., Christensen, E. I., 1992, Handbook of physiology: Renal Physiology, Windhager, editor, New York, Oxford University Press, 42-207
Non-Patent Document 4: Flavia F. J., Julie R. I. et al., 1998, Kidney International, 53, 358-366
Non-Patent Document 5: Zou, Z., Biemesderfer D. et al., 2004, J. Biol. Chem. 279 (33) 34302-34310
Non-Patent Document 6: Biemesderfer, D., 2006, Kidney Int. 69 (10), 1717-1721
Non-Patent Document 7: Li, Y., Biemesderfer, D. et al., 2008, Am. J. Physiol. Cell. Physiol. 295 (2) C529-537
Non-Patent Document 8: Xia, W., Wolfe, M. S., 2003, J. Cell. Sci. 116 (Pt14), 2839-2844

DISCLOSURE OF THE INVENTION

The present invention is intended to provide a diagnostic kit and a diagnostic marker used for diagnosis of a renal disease. Also, the present invention is intended to provide a method for diagnosing a renal disease using human megalin in urine as an indicator for diagnosis in the form of a diagnostic marker for a renal disease. In addition, the present invention is intended to provide a method for evaluating effects of treating a renal disease.

The present inventors have reported a method for measuring the amount of megalin excreted into the urine in the past (WO 2007/119563). However, they have not yet succeeded in evaluating patterns of human megalin subjected to cleavage modification (e.g., shedding) by a protease in vivo and excreted into the urine. Thus, the technique disclosed in WO 2007/119563 was insufficient to completely understand the pathological conditions of a renal disease.

The present inventors have conducted concentrated studies in order to attain the above objects; i.e., complete understanding of pathological conditions of a renal disease. As a result, they discovered that measurement of the amount of megalin excreted into the urine and differential evaluation of patterns of human megalin excreted into the urine via three types of methods for measuring human megalin would enable recognition and analysis of all information regarding changes in the pathological conditions of a renal disease. They also discovered that human megalin in urine could be utilized for diagnosis of pathological conditions and treatment. The term "three types of methods for measuring human megalin" refers to: a method of measurement with the use of a ligand capable of binding to a human megalin ectodomain in urine; a method of measurement with the use of a ligand capable of binding to full-length human megalin in urine; and a method of measurement with the use of a ligand capable of binding to a human megalin endodomain in urine. Since full-length human megalin comprises an ectodomain and an endodomain, a method of measurement with the use of a ligand capable of binding to an ectodomain enables measurement of full-length human megalin, as well as an ectodomain fragment. Also, a method of measurement with the use of a ligand capable of binding to an endodomain enables measurement of full-length human megalin, as well as an endodomain fragment. Thus, the three types of human megalins in urine are measured by the above methods, the measured value obtained with the use of a ligand capable of binding to full-length human megalin in urine is subtracted from the measured value obtained with the use of a ligand capable of binding to a human megalin ectodomain in urine, and the determined value is designated as the true (net) concentration of a human megalin ectodomain fragment lacking an endodomain in urine. The measured value obtained with the use of a ligand capable of binding to full-length human megalin in urine is subtracted from the measured value obtained with the use of a ligand capable of binding to a human megalin endodomain in urine, and the determined value is designated as the true (net) concentration of a human megalin endodomain fragment lacking an ectodomain in urine. By the shedding mechanism, human megalin is cleaved and degraded by two different specific cleavage enzymes at two domains (i.e., an ectodomain in the vicinity of a cell membrane and a transmembrane domain in the cell membrane), and a human megalin ectodomain fragment lacking an endodomain and a human megalin endodomain fragment lacking an ectodomain are formed as cleavage/degradation products. Also, full-length human megalin is formed in vivo by cytoplasmic shedding. Specifically, the present inventors discovered that full-length human megalin would be excreted into the urine independently of the shedding mechanism described above. That is, three types of human megalins; i.e., a human megalin ectodomain fragment, a human megalin endodomain fragment, and full-length human megalin, may be excreted into the urine. Thus, the present inventors discovered that three types of human megalins (i.e., the above cleavage products and full-length human megalin) would be excreted into the urine. In addition, the present inventors discovered that excretion dynamics of such three types of human megalins into the urine would be effective for early diagnosis and recognition of pathological conditions of a renal disease. These three types of human megalins in urine can serve as indicators for recognition of pathological conditions of a renal disease with independent clinical significance.

Specifically, the present invention is as follows.

[1] A method for detecting a renal disease comprising measuring at least one type of human megalin existing in urine, which is selected from among full-length human megalin and human megalin fragments of (i) to (iii) below:

(i) full-length human megalin;
(ii) a human megalin endodomain fragment lacking a human megalin ectodomain; and
(iii) a human megalin ectodomain fragment lacking a human megalin endodomain.

[2] A method for detecting a renal disease comprising measuring full-length human megalin and human megalin fragments of (i) to (iii) below existing in urine and analyzing patterns of full-length human megalin and human megalin fragments of (i) to (iii) excreted into the urine:

(i) full-length human megalin;
(ii) a human megalin endodomain fragment lacking a human megalin ectodomain; and
(iii) a human megalin ectodomain fragment lacking a human megalin endodomain.

[3] The method for detecting a renal disease according to [1] or [2], wherein the full-length human megalin consists of a sequence of amino acids 26 to 4655 of the amino acid sequence as shown in SEQ ID NO: 2.

[4] The method for detecting a renal disease according to [1] or [2], wherein the human megalin endodomain fragment consists of the whole or part of a sequence of amino acids 4362 to 4655 or amino acids 4438 to 4655 of the amino acid sequence as shown in SEQ ID NO: 2.

[5] The method for detecting a renal disease according to [1] or [2], wherein the human megalin ectodomain fragment consists of the whole or part of a sequence of amino acids 26 to 4361, amino acids 26 to 314, or amino acids 4362 to 4437 of the amino acid sequence as shown in SEQ ID NO: 2.

[6] The method for detecting a renal disease according to any of [1] to [5] comprising allowing the first ligand capable of binding to human megalin bound to a solid support to react with a urine specimen, allowing the second ligand capable of binding to human megalin to react with a urine specimen, and measuring the amount of the second ligand capable of binding to human megalin bound to a solid support upon formation of a complex of human megalin in the urine specimen and a ligand capable of binding to human megalin or allowing a urine specimen to react with a ligand capable of binding to human megalin bound to a particle to cause an immunoagglutination reaction and measuring human megalin based on the resulting agglutination.

[7] The method for detecting a renal disease according to [6], wherein the first ligand is an antibody recognizing a human megalin ectodomain fragment consisting of a sequence of amino acids 26 to 4361 or amino acids 26 to 314 of the amino acid sequence as shown in SEQ ID NO: 2 and the second ligand is an antibody recognizing a human megalin endodomain fragment consisting of a sequence of amino acids 4438 to 4655 or amino acids 4447 to 4655 of the amino acid sequence as shown in SEQ ID NO: 2, or the first ligand is an antibody recognizing a human megalin endodomain fragment consisting of a sequence of amino acids 4438 to 4655 or amino acids 4447 to 4655 of the amino acid sequence as shown in SEQ ID NO: 2 and the second ligand is an antibody recognizing a human megalin ectodomain fragment consisting of a sequence of amino acids 26 to 4361 or amino acids 26 to 314 of the amino acid sequence as shown in SEQ ID NO: 2.

[8] The method for detecting a renal disease according to [6], wherein the first ligand and the second ligand are two different antibodies independently recognizing a human megalin endodomain fragment consisting of a sequence of amino acids 4362 to 4655, two different antibodies independently recognizing a human megalin endodomain fragment consisting of a sequence of amino acids 4438 to 4655, or two different antibodies independently recognizing a human megalin endodomain fragment consisting of a sequence of amino acids 4447 to 4655 of the amino acid sequence as shown in SEQ ID NO: 2.

[9] The method for detecting a renal disease according to [6], wherein the first ligand and the second ligand are two different antibodies independently recognizing a human megalin endodomain fragment consisting of a sequence of amino acids 26 to 4361, two different antibodies independently recognizing a human megalin endodomain fragment consisting of a sequence of amino acids 26 to 314, or two different antibodies independently recognizing a human megalin ectodomain fragment consisting of a sequence of amino acids 4362 to 4437 of the amino acid sequence as shown in SEQ ID NO: 2.

[10] The method for detecting a renal disease according to any of [1] to [9], wherein the true measured value for the human megalin endodomain fragment lacking a human megalin ectodomain in urine is obtained by subtracting the measured value for full-length human megalin from the measured value obtained with the use of a ligand capable of binding to the human megalin endodomain fragment lacking a human megalin ectodomain.

[11] The method for detecting a renal disease according to any of [1] to [9], wherein the true measured value for the human megalin ectodomain fragment lacking a human megalin endodomain in urine is obtained by subtracting the measured value for full-length human megalin from the measured value obtained with the use of a ligand capable of binding to the human megalin ectodomain fragment lacking a human megalin endodomain.

[12] The method for detecting a renal disease according to any of [1] to [11], wherein the measured value obtained with the use of a ligand capable of binding to a human megalin endodomain fragment lacking a human megalin ectodomain is regarded as a true measured value for a human megalin endodomain fragment lacking a human megalin ectodomain in urine.

[13] The method for detecting a renal disease according to any of [1] to [11], wherein the measured value obtained with the use of a ligand capable of binding to a human megalin ectodomain fragment lacking a human megalin endodomain is regarded as a true measured value for a human megalin ectodomain fragment lacking a human megalin endodomain in urine.

[14] A marker for detecting a renal disease comprising any of full-length human megalin and human megalin fragments of (i) to (iii) below:
(i) full-length human megalin;
(ii) a human megalin endodomain fragment lacking a human megalin ectodomain; and
(iii) a human megalin ectodomain fragment lacking a human megalin endodomain.

This description includes part or all of the contents as disclosed in the description and/or drawings of Japanese Patent Application No. 2009-108498, which is a priority document of the present application.

PREFERRED EMBODIMENTS OF THE INVENTION

Figure 1:
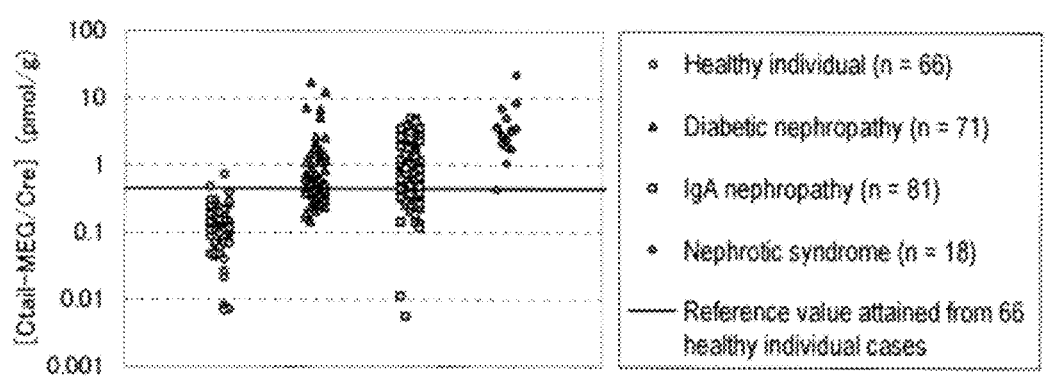
FIG. 1 shows the results of measurement of the amount of human megalin comprising an endodomain excreted into the urine (creatinine correction value) in cases of type II diabetic nephropathy (71 cases), IgA nephropathy (81 cases), and nephrotic syndrome (18 cases).

Hereafter, the present invention is described in detail.

In the present invention, full-length human megalin comprises a sequence of amino acids 26 to 4655 of the amino acid sequence as shown in SEQ ID NO: 2. SEQ ID NO: 1 shows the nucleotide sequence of human megalin. The sequence of amino acids 1 to 25 of the amino acid sequence as shown in SEQ ID NO: 2 is a signal peptide sequence. The amino acid sequence of human megalin is disclosed under Accession No: NP_004516 (RefSeq protein ID: 126012573) in the National Center for Biotechnology Information (NCBI).

Human megalin is a single-pass transmembrane glycoprotein composed of three domains: an ectodomain (extracellular domain); a transmembrane domain; and an endodomain (intracellular domain). In the present invention, the term "human megalin endodomain" refers to a cytoplasmic domain located inside the cell membrane when human megalin is expressed on a cell membrane in the form of a cell transmembrane glycoprotein. A domain consisting of amino acids 4447 to 4655 of the amino acid sequence as shown in SEQ ID NO: 2 is referred to as a human megalin endodomain. Similarly, a domain consisting of amino acids 4425 to 4446 of the amino acid sequence as shown in SEQ ID NO: 2 is referred to as a human megalin transmembrane domain. In addition, a domain consisting of amino acids 26 to 4424 of the amino acid sequence as shown in SEQ ID NO: 2 is referred to as a human megalin ectodomain. In the present invention, the term "human megalin endodomain fragment" refers to a fragment comprising the entire endodomain, which is the whole or part of a domain consisting of amino acids 4362 to 4655 of the amino acid sequence as shown in SEQ ID NO: 2 and lacks a major part of ectodomain. When the human endo-domain fragment is limited to a domain consisting of amino acids 4438 to 4655 of the amino acid sequence as shown in SEQ ID NO: 2, further, the fragment completely lacks an ectodomain. The term "human megalin ectodomain fragment" refers to a fragment comprising the whole or part of an ectodomain, which is the whole or part of a domain consisting of amino acids 26 to 4424 of the amino acid sequence as shown in SEQ ID NO: 2 and lacks an endodomain.

A human megalin endodomain fragment lacking an ectodomain is a transient cleavage product resulting from cleavage of a full-length human megalin sequence by metalloprotease, and it is a transmembrane protein. An example of a human megalin endodomain fragment lacking an ectodomain is a fragment consisting of amino acids 4362 to 4655 of the amino acid sequence as shown in SEQ ID NO: 2. Further, an example of a human megalin endodomain fragment lacking an ectodomain is a fragment consisting of a sequence of amino acids 4438 to 4655 of the amino acid sequence as shown in SEQ ID NO: 2. Such fragment is a secondary cleavage product resulting from further cleavage of a primary cleavage product consisting of amino acids 4362 to 4655 of the amino acid sequence as shown in SEQ ID NO: 2 by γ-serectase.

An example of a human megalin ectodomain fragment lacking an endodomain is a fragment consisting of a sequence of amino acids 26 to 4361 of the amino acid sequence as shown in SEQ ID NO: 2. Such fragment is a remnant ectodomain fragment generated during a process of preparation of the primary cleavage product consisting of amino acids 4362 to 4655 of the amino acid sequence as shown in SEQ ID NO: 2. A further example of a human megalin ectodomain fragment lacking an endodomain is a fragment consisting of a sequence of amino acids 4362 to 4437 of the amino acid sequence as shown in SEQ ID NO: 2. Such fragment is a remnant ectodomain fragment generated during a process of preparation of the secondary cleavage product consisting of amino acids 4438 to 4655 of the amino acid sequence as shown in SEQ ID NO: 2.

Full-length human megalin, an endodomain fragment as a primary cleavage product, an endodomain fragment as a secondary cleavage product, and a remnant ectodomain fragment generated from full-length human megalin during the processes of primary and secondary cleavage product formation may occasionally include some mutations depending on individual subject. Accordingly, mutants of full-length human megalin of the present invention, an endodomain fragment as a primary cleavage product, an endodomain fragment as a secondary cleavage product, and a remnant ectodomain fragment generated from full-length human megalin during the processes of primary and secondary cleavage product formation are within the scope of the present invention.

Amino acid sequence identity between a mutant sequence and the original protein or peptide sequence is not particularly limited. Examples of the amino acid sequence of full-length human megalin of the present invention include amino acid sequences derived from a sequence of amino acids 26 to 4655 of the amino acid sequence as shown in SEQ ID NO: 2 by mutation, such as deletion, substitution, or addition, of at least 1 and preferably 1 or several amino acids. In the present invention, the expression "1 or several" refers to 1 to 10, preferably 1 to 5, and further preferably 4, 3, 2, or 1. An example of an amino acid sequence derived from a sequence of amino acids 26 to 4655 of the amino acid sequence as shown in SEQ ID NO: 2 by mutation, such as deletion, substitution, or addition, of at least 1 and preferably 1 or several amino acids, is a sequence having at least 85%, preferably at least 90%, further preferably 95%, and particularly preferably at least 97% sequence identity with the sequence of amino acids 26 to 4655 of the amino acid sequence as shown in SEQ ID NO: 2, when calculated via BLAST or via other means (e.g., with the use of default, or initially set, parameters).

Examples of the human megalin endodomain fragment of the present invention include amino acid sequences derived from a sequence of amino acids 4362 to 4655 of the amino acid sequence as shown in SEQ ID NO: 2 and from a sequence of amino acids 4438 to 4655 of the amino acid sequence as shown in SEQ ID NO: 2 by mutation, such as deletion, substitution, or addition, of at least 1 and preferably 1 or several amino acids. In the present invention, the expression "1 or several" refers to 1 to 10, preferably 1 to 5, and further preferably 4, 3, 2, or 1. Examples of amino acid sequences derived from a sequence of amino acids 4362 to 4655 of the amino acid sequence as shown in SEQ ID NO: 2 and a sequence of amino acids 4438 to 4655 of the amino acid sequence as shown in SEQ ID NO: 2 by mutation, such as deletion, substitution, or addition, of at least 1 and preferably 1 or several amino acids include sequences having at least 85%, preferably at least 90%, further preferably 95%, and particularly preferably at least 97% sequence identity with a sequence of amino acids 4362 to 4655 of the amino acid sequence as shown in SEQ ID NO: 2 and a sequence of amino acids 4438 to 4655 of the amino acid sequence as shown in SEQ ID NO: 2, when calculated with the use of BLAST or other means (e.g., with the use of default, or initially set, parameters).

Further, examples of the human megalin ectodomain fragment of the present invention include fragments derived from a sequence of amino acids 26 to 4361 of the amino acid sequence as shown in SEQ ID NO: 2 and a sequence of amino acids 4362 to 4437 of the amino acid sequence as shown in SEQ ID NO: 2 by mutation, such as deletion, substitution, or addition, of at least 1 and preferably 1 or several amino acids. In the present invention, the expression "1 or several" refers to 1 to 10, preferably 1 to 5, and further preferably 4, 3, 2, or 1. Examples of amino acid sequences derived from a sequence of amino acids 26 to 4361 of the amino acid sequence as shown in SEQ ID NO: 2 and a sequence of amino acids 4362 to 4437 of the amino acid sequence as shown in SEQ ID NO: 2 by mutation, such as deletion, substitution, or addition, of at least 1 and preferably 1 or several amino acids include sequences having at least 85%, preferably at least 90%, further preferably 95%, and particularly preferably at least 97% sequence identity with a sequence of amino acids 26 to 4361 of the amino acid sequence as shown in SEQ ID NO: 2 and a sequence of amino acids 4362 to 4437 of the amino acid sequence as shown in SEQ ID NO: 2, when calculated with the use of BLAST or via other means (e.g., with the use of default, or initially set, parameters).

Full-length human megalin, the human megalin endodomain fragment lacking an ectodomain, and the human megalin ectodomain fragment lacking an endodomain mentioned above can be measured with the use of a ligand capable of binding to full-length human megalin, a human megalin endodomain fragment lacking an ectodomain, or a human megalin ectodomain fragment lacking an endodomain. In the present invention, specifically, full-length human megalin excreted into and present in urine, a human megalin endodomain fragment excreted into and present in urine, and a human megalin ectodomain fragment excreted into and present in urine are measured. In the present invention, measurement is carried out with the use of a ligand capable of binding to human megalin. In such a case, measured values can be independently attained by measurement with the use of a ligand capable of binding to a human megalin endodomain fragment, measurement with the use of a ligand capable of binding to a human megalin ectodomain fragment, and measurement with the use of a ligand capable of binding to full-length human megalin. Measurement can be carried out in accordance with, for example, WO 2007/119563.

For example, measurement with the use of a ligand capable of binding to full-length human megalin can be carried out with the use of the first ligand capable of binding to full-length human megalin bound to a solid support and the second ligand capable of binding to full-length human megalin by allowing the first ligand capable of binding to full-length human megalin bound to a solid support to react with a specimen, allowing the second ligand capable of binding to full-length human megalin to react with a specimen, and then measuring the second ligand capable of binding to full-length human megalin bound to a solid support upon formation of a complex of full-length human megalin in the specimen and a ligand capable of binding to full-length human megalin. When an endodomain fragment and an ectodomain fragment are present in urine in addition to full-length human megalin and both the first and the second binding ligands bind to the ectodomain fragment or when both the first and the second binding ligands bind to the endodomain fragment, the endodomain fragment or ectodomain fragment is measured, in addition to the full-length human megalin. In order to selectively measure a full-length fragment, accordingly, it is necessary to select ligands, so that the first ligand and the second ligand bind to fragments of different domains. When the first ligand binds to an endodomain fragment, specifically, the second ligand should be capable of binding to an ectodomain fragment. When the first ligand binds to an ectodomain fragment, the second ligand should be capable of binding to an endodomain fragment.

Measurement with the use of a ligand capable of binding to a human megalin endodomain fragment lacking an ectodomain can be carried out with the use of the first ligand capable of binding to a human megalin endodomain fragment bound to a solid support and the second ligand capable of binding to a human megalin endodomain fragment by allowing the first ligand capable of binding to a human megalin endodomain fragment bound to a solid support to react with a specimen, allowing the second ligand capable of binding to the human megalin endodomain fragment to react with the specimen, and then measuring the second ligand capable of binding to an endodomain fragment bound to a solid support upon formation of a complex of a human megalin endodomain fragment in the specimen and a ligand capable of binding to the human megalin endodomain fragment. When full-length human megalin is present in urine, both the full-length human megalin and the human megalin endodomain fragment lacking an ectodomain are to be measured. Thus, measurement with the use of a ligand capable of binding to a human megalin endodomain fragment lacking an ectodomain may be regarded as the measurement of the human megalin comprising an endodomain. A fragment comprising at least an endodomain and full-length human megalin are also within the scope of the "human megalin comprising an endodomain" according to the present invention. Accordingly, the true (net) value for the endodomain fragment is a value obtained by subtracting the measured value for full-length human megalin from the measured value obtained with the use of a ligand capable of binding to the human megalin endodomain fragment. The measured value obtained with the use of a ligand capable of binding to the human megalin endodomain fragment may be employed as the true (net) value for the endodomain fragment for renal-disease-associated evaluation, such as detection of a renal disease. In the present invention, performance of renal-disease-associated evaluation, such as detection of a renal disease, using the measured value obtained with the use of a ligand capable of binding to the human megalin endodomain fragment as the true (net) value for the endodomain fragment may be occasionally referred to as approximate evaluation with the use of the measured value obtained with the use of a ligand capable of binding to the human megalin endodomain fragment.

Measurement with the use of a ligand capable of binding to a human megalin ectodomain fragment lacking an endodomain can be carried out with the use of the first ligand capable of binding to the human megalin ectodomain fragment bound to a solid support and the second ligand capable of binding to the human megalin ectodomain fragment by allowing the first ligand capable of binding to the human megalin ectodomain fragment bound to a solid support to react with a specimen, allowing the second ligand capable of binding to the human megalin ectodomain fragment to react with the specimen, and then measuring the second ligand capable of binding to the ectodomain fragment bound to a solid support upon formation of a complex of a human megalin ectodomain fragment in the specimen and a ligand capable of binding to the human megalin ectodomain fragment. When full-length human megalin is present in urine, both the full-length human megalin and the human megalin ectodomain fragment lacking an endodomain are to be measured. Thus, measurement with the use of a ligand capable of binding to a human megalin ectodomain fragment lacking an endodomain may be regarded as measurement of the human megalin comprising an ectodomain. A fragment comprising at least an ectodomain and full-length human megalin are also within the scope of "human megalin comprising an ectodomain" according to the present invention. Accordingly, the true (net) value for the ectodomain fragment is obtained by subtracting the measured value for full-length human megalin from the measured value obtained with the use of a ligand capable of binding to the human megalin ectodomain fragment. The measured value obtained with the use of a ligand capable of binding to the human megalin ectodomain fragment may be employed as the true (net) value for the ectodomain fragment for renal-disease-associated evaluation, such as detection of a renal disease. In the present invention, performance of renal-disease-associated evaluation, such as detection of a renal disease, using the measured value obtained with the use of a ligand capable of binding to the human megalin ectodomain fragment as the true (net) value for the ectodomain fragment may be occasionally referred to as approximate evaluation with the use of the measured value obtained with the use of a ligand capable of binding to the human megalin ectodomain fragment.

In such technique, the full-length human megalin, human megalin endodomain fragment lacking an ectodomain, or human megalin ectodomain fragment lacking an endodomain is sandwiched with the first ligand and the second ligand and assayed. (This technique is referred to as a "sandwich assay.) In such a case, any solid supports used for conventional immunoanalyses can be used. Examples thereof that can be preferably used include wells of a plastic microtiter plate and magnetic particles.

Examples of ligands capable of binding to human megalin include antibodies reacting with full-length human megalin, a human megalin endodomain fragment lacking an ectodomain, and a human megalin ectodomain fragment lacking an endodomain. A monoclonal or polyclonal antibody can be used. An anti-human megalin antibody used for immobilization or labeling may be an immunoglobulin fragment specific to full-length human megalin, a human megalin endodomain fragment lacking an ectodomain, or a human megalin ectodomain fragment lacking an endodomain, such as Fab or F(ab')$_2$, or recombinant antibody, such as scFv, dsFv, diabody, or minibody. The term "antibody" used in the present invention also refers to a fragment specific to full-length human megalin, a human megalin endodomain fragment lacking an ectodomain, or a human megalin ectodomain fragment lacking an endodomain. A method for preparing such fragment is well-known in the art.

When measurement is carried out with the use of ligands capable of binding to a human megalin endodomain fragment lacking an ectodomain, two types of antibodies, one independently recognizing a human megalin endodomain fragment lacking an ectodomain and the other recognizing a different epitope, may be used as the first ligand and the second ligand. Examples thereof include two types of antibodies, one independently recognizing an endodomain consisting of amino acids 4447 to 4655 of the amino acid sequence as shown in SEQ ID NO: 2 and recognizing a different epitope. When measurement is carried out with the use of a ligand capable of binding to a human megalin ectodomain fragment lacking an endodomain, two types of antibodies, one independently recognizing a human megalin ectodomain fragment lacking an endodomain and the other recognizing a different epitope, may be used as the first ligand and the second ligand. Examples thereof that can be used include two types of antibodies, one independently recognizing an ectodomain consisting of amino acids 26 to 4361 of the amino acid sequence as shown in SEQ ID NO: 2 and recognizing a different epitope. When measurement is carried out with the use of a ligand capable of binding to full-length human megalin, an antibody recognizing an epitope of a human megalin endodomain fragment lacking an ectodomain and an antibody recognizing another epitope of a human megalin endodomain fragment lacking an ectodomain may be used as two types of ligands.

The second ligand is labeled with an enzyme, fluorescence, biotin, or radioactive label to prepare an enzyme-labeled ligand, and the label is subjected to measurement. Thus, the second ligand capable of binding to human megalin bound to a solid support can be measured. Labeling with an enzyme or fluorescence is particularly preferable. Examples of enzymes include, but are not limited to, peroxidase, alkaline phosphatase, β-galactosidase, and glucose oxidase. An example of fluorescence is fluorescein isothiocyanate (FITC), although fluorescence is not limited thereto. Labeling can be detected by allowing a corresponding substrate to react with an enzyme-labeled ligand and measuring a pigment, fluorescence, luminescence, or the like resulting from the reaction. The above method comprises two steps of: allowing the first ligand bound to a solid support to react with a specimen, followed by washing, and then allowing the second ligand to react therewith. Alternatively, a step of allowing the first ligand bound to a solid support to react with a specimen and a step of allowing a specimen to react with the second ligand may be carried out simultaneously as a single step.

Further, the present invention includes a method for measuring full-length human megalin, a human megalin endodomain fragment lacking an ectodomain, or a human megalin ectodomain fragment lacking an endodomain in a specimen with the use of a ligand capable of binding to full-length human megalin, a human megalin endodomain fragment lacking an ectodomain, or a human megalin ectodomain fragment lacking an endodomain. The method comprises allowing a specimen to react with a ligand capable of binding to full-length human megalin, a human megalin endodomain fragment lacking an ectodomain, or a human megalin ectodomain fragment lacking an endodomain bound to a particle to cause an agglutination reaction and measuring the full-length human megalin, the human megalin endodomain fragment lacking an ectodomain, or the human megalin ectodomain fragment lacking an endodomain based on the degree of the resulting agglutination. Examples of particles used in such method include latex particles having a diameter of 0.05 to 10 μm and preferably 0.1 to 0.4 μm and gelatin particles and animal blood erythrocytes having a diameter of 0.5 to 10 μm. A method of binding an antibody to a particle is well-known in the art, and it may be physical adsorption or covalent binding. In the above described method, a particle to which a ligand, such as an antibody reacting with full-length human megalin, a human megalin endodomain fragment lacking an ectodomain, or a human megalin ectodomain fragment lacking an endodomain, has been bound is mixed with the specimen on, for example, a black-colored glass slide, and particle precipitation upon agglutination is observed. Thus, full-length human megalin, a human megalin endodomain fragment lacking an ectodomain, or a human megalin ectodomain fragment lacking an endodomain in urine can be detected. By measuring the absorbance of such agglutination, full-length human megalin, a human megalin endodomain fragment lacking an ectodomain, or a human megalin ectodomain fragment lacking an endodomain can be quantified. Further, detection can be carried out via pulse immunoassay.

The measured value obtained with the use of a ligand binding to full-length human megalin in urine is limited to the value for full-length human megalin; however, the measured value obtained with the use of a ligand binding to a human megalin endodomain fragment lacking an ectodomain is the sum of the measured value for full-length human megalin and that for the endodomain fragment, when full-length human megalin is present in urine. The measured value obtained with the use of a ligand binding to a human megalin ectodomain fragment lacking an endodomain is the sum of the measured value for full-length human megalin and that for the ectodomain fragment, when full-length human megalin is present in urine. The true (net) content of the human megalin endodomain fragment lacking an ectodomain is determined by subtracting the measured value for full-length human megalin from that for the human megalin endodomain fragment lacking an ectodomain. Similarly, the true content of the human megalin ectodomain fragment lacking an endodomain is determined by subtracting the measured value for full-length human megalin from that for the human megalin ectodomain fragment lacking an endodomain.

According to the method of the present invention, full-length human megalin, a human megalin endodomain fragment lacking an ectodomain, or a human megalin ectodomain fragment lacking an endodomain in urine can be measured. Based on the measured values, dynamics of three types of human megalins excreted into the urine can be determined. In addition, a renal disease can be detected based on the measured value for the full-length human megalin, a human megalin endodomain fragment lacking an ectodomain, or a human megalin ectodomain fragment lacking an endodomain in urine, and such detection enables early diagnosis and recognition of pathological conditions. Further, such detection enables prognostic prediction of a renal disease and evaluation of the degree of disorder at an early stage of nephropathy. Examples of renal diseases that can be detected by the present invention include type II diabetic nephropathy and IgA nephropathy.

In addition, patterns for each human megalin excreted into the urine can be determined based on the measured values for full-length human megalin, a human megalin endodomain fragment lacking an ectodomain, and a human megalin ectodomain fragment lacking an endodomain in urine. In the present invention, such excretion patterns are referred to as three patterns of human megalin excretion into the urine, and dynamics of human megalin excretion into the urine can be analyzed based on these patterns. The analysis of excretion dynamics enables detection, early diagnosis, and recognition of pathological conditions of a renal disease. In addition, such analysis enables prognostic prediction and evaluation of the degree of disorder of a renal disease at an early stage of nephropathy.

In the present invention, detection of a renal disease includes detection, early diagnosis, and recognition of pathological conditions of a renal disease, prognostic prediction of a renal disease, and evaluation of the degree of disorder at the phase of preceding stage of nephropathy.

When the amount of full-length human megalin, a human megalin endodomain fragment lacking an ectodomain, or a human megalin ectodomain fragment lacking an endodomain excreted into the urine is large, for example, the severity of a renal disease can be judged to be high, and a patient may be evaluated as having a poor prognosis.

In such a case, the measured value obtained with the use of a ligand capable of binding to the human megalin endodomain fragment may be employed as the true (net) value for the endodomain fragment for approximate evaluation associated with a renal disease, such as detection of a renal disease. In addition, approximate evaluation associated with a renal disease, such as detection of a renal disease, can be performed using the measured value obtained with the use of a ligand capable of binding to the human megalin ectodomain fragment as the true (net) value for the ectodomain fragment.

Megalin excretion into the urine reflects the integrated results of the expression level of megalin in renal tissue and the degree of deviation from renal tissue. The amount of megalin excreted increases as renal-disease-associated tubular dysfunctions advance; however, the megalin expression level in tissue decreases as the disease advances. Further, the increased amount of ectodomain fragment excretion is caused by a compensatory factor. In the case of full-length megalin or an endodomain fragment, there is no compensatory factor, and the normal excretion levels are considered to differ depending on disease stage or disease type. In the case of an ectodomain fragment, however, healthy individuals can experience certain levels of normal excretion. If the stage of a healthy individual advances to a hyperfunctional stage, the excretion levels thereof exceed the aforementioned normal levels. Those exhibiting excretion levels exceeding such normal levels are highly likely to be at a high risk of disease advancement, and such individuals can be evaluated as being likely to experience an advanced stage. Thus, populations of healthy individuals are not different from disease groups in terms of ectodomain fragment behavior. Cases of individual patients exhibiting values exceeding the reference value can be evaluated as being at a high risk of disease advancement. This is the greatest advantage of analysis of the dynamics of ectodomain fragment excretion.

EXAMPLES

The present invention is described in detail with reference to the following examples, although the present invention is not limited to these examples.

Example 1

Preparation of Mouse Anti-Human Megalin Monoclonal Antibody

A domain consisting of amino acids 26 to 314 of the amino acid sequence as shown in SEQ ID NO: 2 (hereafter abbreviated as "LBD1") was prepared in the form of an immunogen used for preparation of an anti-human megalin ectodomain monoclonal antibody via an E. coli recombinant technique. Also, a domain consisting of amino acids 4447 to 4655 of the amino acid sequence as shown in SEQ ID NO: 2 (hereafter abbreviated as "Ctail") was prepared in the form of an immunogen used for preparation of an anti-human megalin endodomain monoclonal antibody via an E. coli recombinant technique. A mouse was immunized with the resulting recombinant LBD1 or Ctail antigen.

A mouse was intraperitoneally immunized with 50 μg of the recombinant LBD1 antigen or 50 μg of the recombinant Ctail antigen and an adjuvant several times, and the elevated serum titer thereof was confirmed. The spleen was extracted 3 days after booster immunization (in the vein) to obtain splenic cells. The obtained suplenic cells were fused to mouse myeloma cells (10:1) in the presence of polyethylene glycol 3500 to prepare hybridoma cells. The resulting cells were cultured in $CO_2$ at 37° C. for 1 week, and the presence of anti-human megalin antibodies in the culture supernatant was inspected. The cells in positive wells in which antibody production was observed were diluted via limiting dilution, the resultant was cultured for 2 weeks, and the presence of anti-human megalin antibodies in the culture supernatant was inspected in the same manner. Further, cells in positive wells in which antibody production was observed were subjected to limiting dilution again and culture was conducted in the same manner. Cells in which anti-human megalin antibodies had already been produced at this phase were cultured in a flask, some of the resultant was suspended in fetal calf serum (FCS) containing 10% dimethyl sulfoxide (DMSO) ($5 \times 10^6$ cells/ml), and the resultant was stored in liquid nitrogen.

Subsequently, supernatants in the wells were used to inspect the reactivity of antibodies produced in the culture supernatant to human megalin. Human megalin was dissolved in 140 mM NaCl, 2.7 mM KCl, 10 mM $Na_2HPO_4$, and 1.8 mM $KH_2PO_4$ (pH 7.3) (hereafter abbreviated as "PBS (pH 7.3)"). The human megalin/PBS (pH 7.3) solution was applied to wells of a plastic microtiter plate (Nunc-Immuno™ Module F8 Maxisorp™ Surface plate, manufactured by Nalge Nunc International) at 100 μl/well, and human megalin was immobilized on the microtiter plate at 3 pmol/well at 4° C. for 12 hours. The human megalin/PBS (pH 7.3) solution that had been applied to the wells was removed via decantation 12 hours later, a wash solution was applied to the wells of the microtiter plate at 200 μl/well, the wash solution was removed via decantation, and human megalin excessively adsorbed in the wells was washed. This process of washing was carried out twice in total. Thereafter, a blocking solution was applied to the antigen-immobilized plate at 200 μl/well to block the wells of the human-megalin-immobilized microtiter plate at 4° C. for 12 hours. Twelve hours later, the plate was stored at 4° C. In order to confirm reactivity of antibodies in the culture supernatant, the human-megalin-immobilized microtiter plate resulting after blocking was used. The hybridoma culture supernatant was applied to wells of the human-megalin-immobilized microtiter plate at 100 μl/well, and the plate was heated at 37° C. for 1 hour. Thereafter, the culture supernatant that had been applied to the wells was removed via decantation, a wash solution was applied to the wells of the microtiter plate at 200 μl/well, the wash solution was removed via decantation, and insides of the wells were washed. This process of washing was carried out three times in total. Thereafter, peroxidase-conjugated goat anti-mouse immunoglobulin (manufactured by DAKO) was applied to the wells at 100 μl/well (2.000-fold diluted, 0.55 μg/ml), and the plate was heated at 37° C. for 1 hour. The enzyme-labeled antibodies were diluted with a diluent for enzyme labeled antibodies. Thereafter, the enzyme-labeled antibodies that had been applied to the wells were removed via decantation, a wash solution was applied to the wells of the microtiter plate at 200 μl/well, the wash solution was removed via decantation, and insides of the wells were washed. This process of washing was carried out three times in total. Thereafter, a solution of 3,3',5,5'-tetramethylbenzidine (hereafter abbreviated as "TMB") (TMB One-Step Substrate System, manufactured by DAKO) was applied to the wells at 100 μl/well as a substrate solution for the peroxidase enzyme reaction, and the resultant was allowed to stand at 25° C. for 30 minutes. Immediately thereafter, a reaction terminator was added to the substrate solution in the wells at 100 μl/well to terminate the enzyme reaction in the wells. Thereafter, the absorbance of the wells was measured, the absorbance at 630 nm was subtracted from that at 450 nm, and the resulting value was designated as an indicator for reactivity evaluation.

As a result, monoclonalized hybridoma cells in which the anti-human megalin antibody exhibited potent reactivity to the immobilized human megalin were selected, and the immunoglobulin class and subclass in the culture supernatant were inspected for each clone from 100 μl of the culture supernatant stock solution using the mouse immunoglobulin typing kit (Wako Pure Chemical Industries, Inc.). Based on the results, cells of the IgG class were selected from the resulting monoclonal cell library and transferred for the process of ascites production described below.

Subsequently, these cells were cultured in a 25-ml flask and further cultured in a 75-ml flask. The resulting cells were injected intraperitoneally into a pristane-treated mouse to sample the ascites.

Example 2

Purification of Anti-Human Megalin Mouse Monoclonal (IgG) Antibody

The obtained ascites (10 ml) was mixed with an opacified blood serum-treating agent (FRIGEN (registered trademark) II: manufactured by Kyowa Pure Chemical Co., Ltd.) at a ratio of 1.5:1 by volume, and the resultant was shaken and stirred for 1 to 2 minutes to delipidize the ascites. The ascites was centrifuged using a centrifuger at 3,000 rpm (1,930×g) for 10 minutes, and the centrifuged supernatant of clarified ascites (10 ml) was fractionated. The centrifuged supernatant of ascites (10 ml) was subjected to ammonium sulfate fractionation (final concentration: 50% saturated ammonium sulfate) in an ice bath for 1 hour, and the precipitated immunoglobulin fraction was suspended and dissolved in PBS. This process of ammonium sulfate fractionation was carried out twice in total to obtain a crude immunoglobulin fraction from ascites. The resulting crude immunoglobulin fraction (10 ml) was mixed with an equivalent amount of 20 mM sodium phosphate (pH 7.0; hereafter referred to as "20 mM NaPB (pH7.0)") and then subjected to affinity purification using a protein G column (HiTrap Protein G HP, 5 ml; manufactured by GE Healthcare). The sample was adsorbed on a protein G column, 50 ml of 20 mM NaPB (pH 7.0) was flushed through the protein G column, and contaminants other than IgG in the sample were removed by washing. Thereafter, affinity-adsorbed IgG on the protein G column was eluted with 0.1 M glycine-HCl (pH 2.7), and the elution fraction immediately after elution from the column was neutralized with 1M Tris (hydroxymethyl)aminomethane-HCl (pH 9.0) (hereafter, "Tris(hydroxymethyl)aminomethane" is abbreviated as "Tris") and then recovered. After neutralization, the affinity-purified product was dialyzed against PBS in an amount 500 times greater than that of the purified product by volume at 4° C. for 6 hours, and this process of dialysis was carried out twice in total. The dialysis membrane used for dialysis was a cellulose tube for dialysis (manufactured by Viskase Companies). The resulting IgG elution fraction was designated as a purified anti-human megalin monoclonal antibody and subjected to storage at 4° C. and procedures described below. The process of purification was performed by connecting the aforementioned protein G column to the BioLogic LP System (manufactured by Bio Rad Laboratories) at a constant flow rate of 1 ml/min.

Example 3

Figure 2:
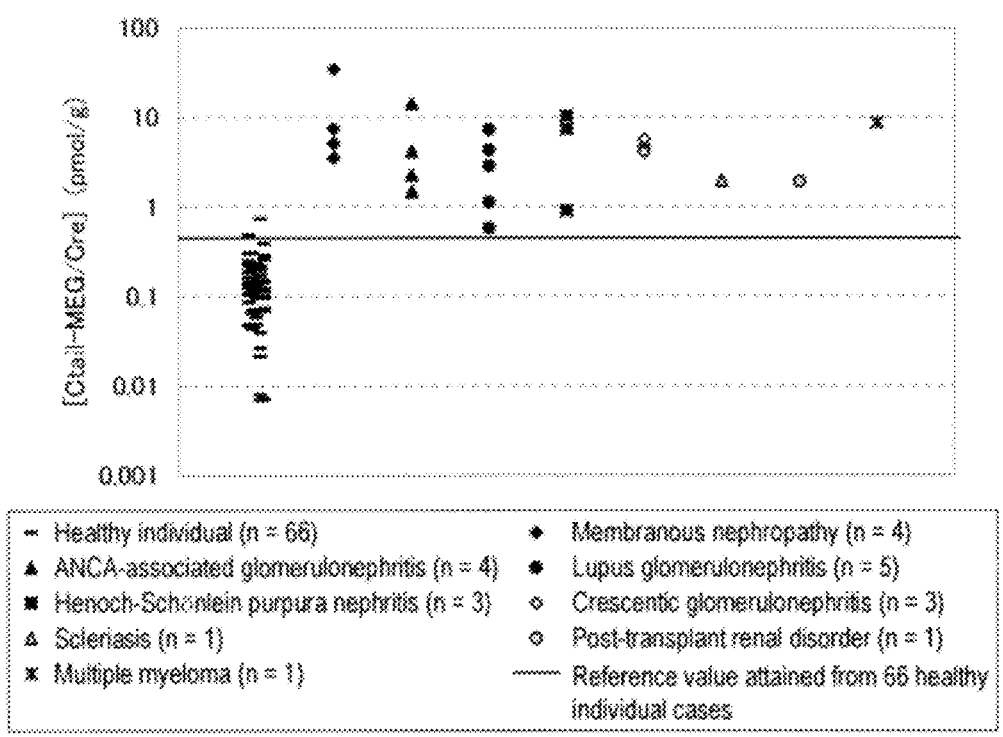
FIG. 2 shows the results of measurement of the amount of human megalin comprising an endodomain excreted into the urine (creatinine correction value) in several other nephropathy cases.

Measurement of the Amount of Human Megalin Comprising an Endodomain Excreted into the Urine Using a Ligand Capable of Binding to a Human Megalin Endodomain Fragment Lacking an Ectodomain With the use of the anti-human megalin endodomain fragment monoclonal antibody, the amount of human megalin comprising an endodomain excreted into the urine was measured. The anti-human megalin endodomain fragment monoclonal antibody is a mouse monoclonal antibody that recognizes an epitope located in an endodomain (Ctail) consisting of amino acids 4447 to 4655 of the amino acid sequence as shown in SEQ ID NO: 2. The amount of human megalin excreted into the urine was measured and evaluated with the use of the anti-human megalin Ctail monoclonal antibody A and the anti-human megalin Ctail monoclonal antibody B recognizing two different epitopes in Ctail. With the use of a microtiter plate on which the anti-human megalin Ctail monoclonal antibodies A had been immobilized and the ALP-labeled anti-human megalin Ctail monoclonal antibody B, the amount of human megalin comprising an endodomain in urine was measured. At the outset, 90 µl of primitive urine was mixed with 10 µl of a solution comprising 2 M Tris-HCl, 0.2 M ethylenediamine-N,N,N',N'-tetraacetic acid (hereafter abbreviated as "EDTA"), and 10% (vol/vol) polyethylene glycol mono-p-isooctylphenyl ether (hereafter abbreviated as "Triton X-100") (pH 8.0), and 100 µl of the resulting mixture was applied to wells of the microtiter plate on which the anti-human megalin Ctail monoclonal antibodies A had been immobilized (FluoroNunc™ Module F16 Black-Maxisorp™ Surface plate, manufactured by Nalge Nunc International). The resultant was allowed to stand at 37° C. for 1 hour, the urine sample solution that had been applied to the wells was removed via decantation, a wash solution was applied to the wells of the microtiter plate at 200 µl/well, and the wash solution was removed via decantation, followed by washing. The process of washing was carried out three times in total. Thereafter, the solution of ALP-labeled anti-human megalin Ctail monoclonal antibodies B (0.5 ng/ml) was applied at 100 µl/well. The ALP-labeled anti-human megalin Ctail monoclonal antibodies B were prepared in a diluent for labeled antibodies. The resultant was allowed to stand at 37° C. for 1 hour, the solution of ALP-labeled antibodies that had been applied to the wells was removed via decantation, a wash solution was applied to the wells of the microtiter plate at 200 µl/well, and the wash solution was removed via decantation, followed by washing. The process of washing was carried out four times in total. Subsequently, 20 mM Tris-HCl and 1 mM $MgCl_2$ (pH 9.8) (hereafter referred to as an "assay buffer") were applied to wells of the microtiter plate at 200 µl/well, and the assay buffer was removed via decantation, followed by washing. The process of washing was carried out twice in total. Thereafter, CDP-Star (registered trademark) chemiluminescent substrate for alkaline phosphatase ready-to-use (0.4 mM) with Emerald-II™ enhancer (ELISA-Light™ System, manufactured by Applied Biosystems) was applied to the wells as a substrate solution for ALP enzyme reaction at 100 µl/well, and the resultant was allowed to stand at 37° C. for 30 minutes while shielded from light. Immediately thereafter, the accumulated emission intensity of the wells for 1 second was measured, and the resulting value was designated as an indicator for measurement and evaluation of concentration of human megalin comprising an endodomain in urine. The chemiluminescence intensity was measured using the Microplate Luminometer Centro LB960 and MicroWin2000 software (manufactured by Berthold). As the reference sample for the calibration curve, native human megalin extracted from the kidney was used. The results of actual clinical measurement of concentration of human megalin comprising an endodomain in urine are shown in FIG. 1 and FIG. 2. Backgrounds of patients subjected to measurement: patients with type II diabetic nephropathy (71 cases); patients with IgA nephropathy (81 cases); and patients with nephrotic syndrome (18 cases), are shown in Table 1.

TABLE 1

| Parameters | 1: Healthy individual | 2: Type II diabetic nephropathy | 3: IgA nephropathy | 4: Nephrotic syndrome |
|---|---|---|---|---|
| Number (n) | 66 | 71 | 81 | 18 |
| Sexuality (F/M) | 20/46 | 26/45 | 57/24 | 6/12 |
| Age | 31.5 ± 10.3 | 65.5 ± 11.8 | 32.2 ± 10.5 | 52.9 ± 15.3 |
| BMI (kg/m$^2$) | 20.5 ± 1.8 | 25.0 ± 5.5 | 21.0 ± 2.9 | 24.5 ± 2.9 |
| Systolic blood pressure (mmHg) | 108.5 ± 9.8 | 129.3 ± 14.7 | 112.3 ± 13.9 | 117.7 ± 13.1 |
| Diastolic blood pressure (mmHg) | 64.5 ± 7.4 | 77.1 ± 9.8 | 64.9 ± 10.4 | 69.4 ± 8.6 |
| Albumin excreted into the urine (mg/g creatinine in urine) | 4.5 ± 2.5 | 2398.2 ± 8459.5 | 1204.5 ± 3136.5 | 12683.8 ± 17513.4 |
| HbA1c (%) | — | 6.8 ± 1.6 | — | — |
| Fasting blood sugar level (mg/dl) | 75.2 ± 7.7 | 148.4 ± 55.7 | — | — |
| eGFR (ml/min/1.73 m$^2$) | 90.2 ± 15.2 | 67.5 ± 18.7 | 84.0 ± 22.6 | 71.1 ± 23.1 |

Figure 3:
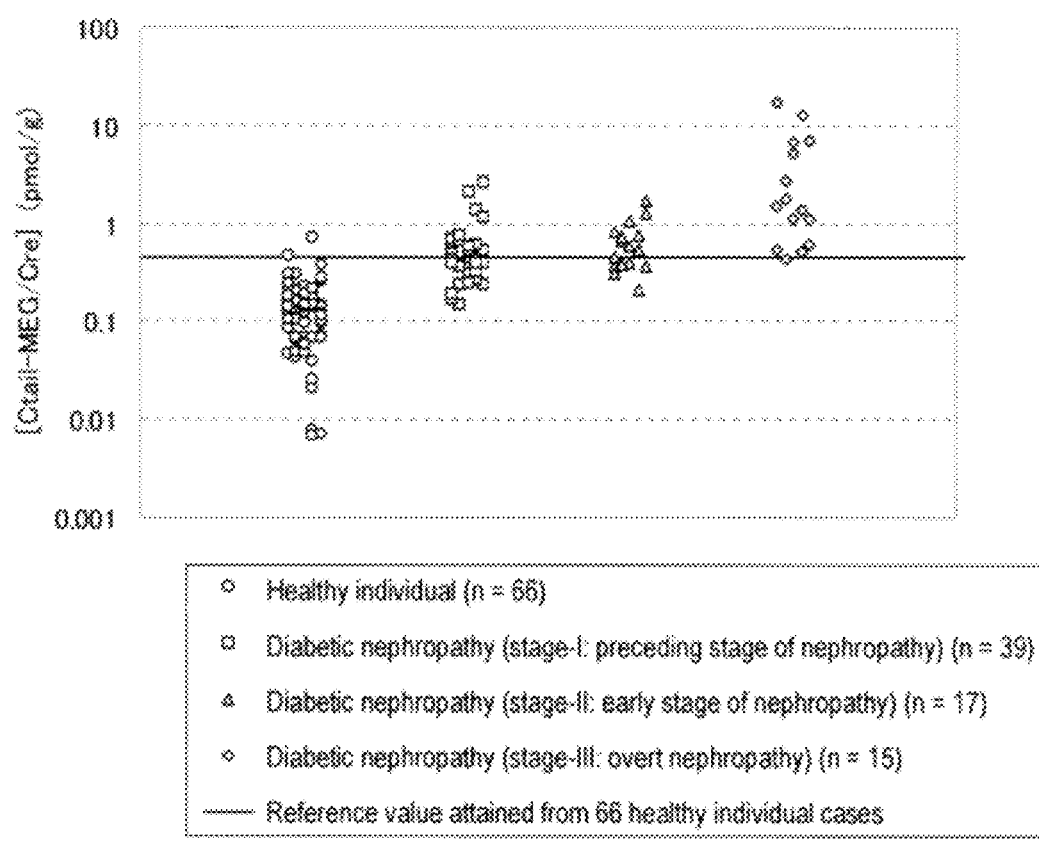
FIG. 3 shows the results of measurement of the amount of human megalin comprising an endodomain excreted into the urine (creatinine correction value) in cases of type II diabetic nephropathy (71 cases) classified in accordance with the degree of albuminuria (classification based on severity of disorder) in accordance with staging of diabetic nephropathy.
Figure 4:
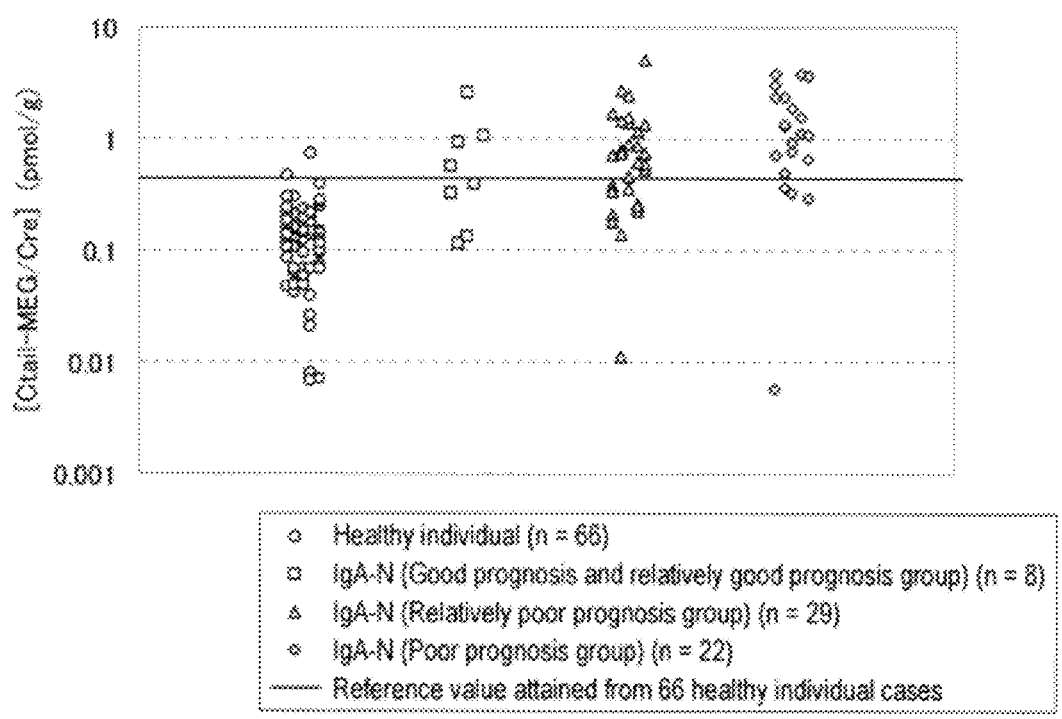
FIG. 4 shows the results of measurement of the amount of human megalin comprising an endodomain excreted into the urine (creatinine correction value) in cases of IgA nephropathy (59 cases) based on histological classification of prognosis (prognosis achieved by histological classification of renal biopsies).

In addition, the correlations between type II diabetic nephropathy or IgA nephropathy and the measured concentration of human megalin comprising an endodomain in urine are shown in FIG. 3 and FIG. 4. Backgrounds of patients with type II diabetic nephropathy (71 cases) and patients with IgA nephropathy (81 cases) are shown in Table 2 and Table 3 in accordance with the severity of pathological conditions.

the severity of type II diabetic nephropathy or prognostic classification of IgA nephropathy (FIGS. 3 and 4). Specifically, the concentration of human megalin comprising an endodomain excreted into the urine was higher in stage I (preceding stage of nephropathy) and stage II (early stage of nephropathy) patients of type II diabetic nephropathy, compared with healthy individuals. Further, it was higher in stage

TABLE 2

| Parameters | 1: Healthy individual | 2: Type II diabetic nephropathy (stage-I: preceding stage ofc nephropathy) | 3: Type II diabetic nephropathy (stage-II: early stage of nephropathy) | 4: Type II diabetic nephropathy (stage-III: overt nephropathy) |
|---|---|---|---|---|
| Number (n) | 66 | 39 | 17 | 15 |
| Sexuality (F/M) | 20/46 | 16/23 | 5/12 | 5/10 |
| Age | 31.5 ± 10.3 | 65.1 ± 12.0 | 63.8 ± 11.7 | 68.7 ± 11.6 |
| BMI (kg/m$^2$) | 20.5 ± 1.8 | 24.4 ± 5.1 | 25.4 ± 6.4 | 26.1 ± 5.7 |
| Systolic blood pressure (mmHg) | 108.5 ± 9.8 | 124.9 ± 10.8 | 134.4 ± 17.4 | 135.5 ± 17.4 |
| Diastolic blood pressure (mmHg) | 64.5 ± 7.4 | 77.8 ± 8.8 | 75.6 ± 12.6 | 76.9 ± 9.4 |
| Albumin excreted into the urine (mg/g creatinine in urine) | 4.5 ± 2.5 | 10.2 ± 6.3 | 87.4 ± 56.4 | 11226.0 ± 15872.8 |
| HbA1c (%) | — | 7.0 ± 1.6 | 6.6 ± 0.9 | 67. ± 2.2 |
| Fasting blood sugar level (mg/dl) | 75.2 ± 7.7 | 74.0 ± 13.8 | 70.1 ± 14.9 | 44.8 ± 19.4 |
| eGFR (ml/min/1.73 m$^2$) | 90.2 ± 15.2 | 74.0 | 70.1 | 44.8 |

TABLE 3

| Parameters | 1: Healthy individual | 2: IgA nephropathy (Good prognosis and relatively good prognosis groups) | 3: IgA nephropathy (Relatively poor prognosis group) | 4: IgA nephropathy (Poor prognosis group) |
|---|---|---|---|---|
| Number (n) | 66 | 8 | 29 | 22 |
| Sexuality (F/M) | 20/46 | 6/2 | 25/4 | 17/5 |
| Age | 31.5 ± 10.3 | 28.3 ± 8.1 | 29.8 ± 6.1 | 34.2 ± 8.6 |
| BMI (kg/m$^2$) | 20.5 ± 1.8 | 20.5 ± 2.6 | 19.5 ± 2.8 | 21.6 ± 2.8 |
| Systolic blood pressure (mmHg) | 108.5 ± 9.8 | 104.0 ± 16.1 | 107.3 ± 8.2 | 118.0 ± 16.6 |
| Diastolic blood pressure (mmHg) | 64.5 ± 7.4 | 57.6 ± 3.6 | 63.1 ± 10.5 | 64.6 ± 12.8 |
| Albumin excreted into the urine (mg/g creatinine in urine) | 4.5 ± 2.5 | 1474.0 ± 2929.6 | 1113.8 ± 3026.9 | 493.4 ± 413.5 |
| HbA1c (%) | — | — | — | — |
| Fasting blood sugar level (mg/dl) | 75.2 ± 7.7 | — | — | — |
| eGFR (ml/min/1.73 m$^2$) | 90.2 ± 15.2 | 105.6 ± 18.0 | 88.6 ± 20.5 | 67.6 ± 19.6 |

As a result, the amount of human megalin comprising an endodomain excreted into the urine was found to have increased significantly in patients with renal diseases, compared with healthy individuals (FIGS. 1 and 2). The amount of megalin excreted into the urine was evaluated with the use of the creatinine correction value determined by dividing the megalin concentration in urine by the creatinine concentration in urine and correcting the concentration. The aforementioned is commonly used as a urinary biomarker in order to verify that the results are not influenced by the concentration rate at the time of urinary excretion. Example 3 demonstrates that concentration of human megalin comprising an endodomain in urine can be specifically measured and evaluated, and the amount of human megalin comprising an endodomain excreted into the urine increases in accordance with III (overt nephropathy) patients than in stage I (preceding stage of nephropathy) and stage II (early stage of nephropathy) patients. When IgA nephropathy patients are classified in accordance with prognostic conditions: i.e., the good prognosis and relatively good prognosis groups; the relatively poor prognosis group; and the poor prognosis group, the concentration of human megalin comprising an endodomain excreted into the urine of patients of such groups is higher than that in healthy individuals. Further, such concentration tends to be higher in patients with poorer prognosis in the order of the good prognosis and relatively good prognosis groups, the relatively poor prognosis group, and the poor prognosis group. It was thus considered that measurement of the concentration thereof would be effective for recognition of pathological conditions and diagnosis of nephropathy.

Example 4

Figure 5:
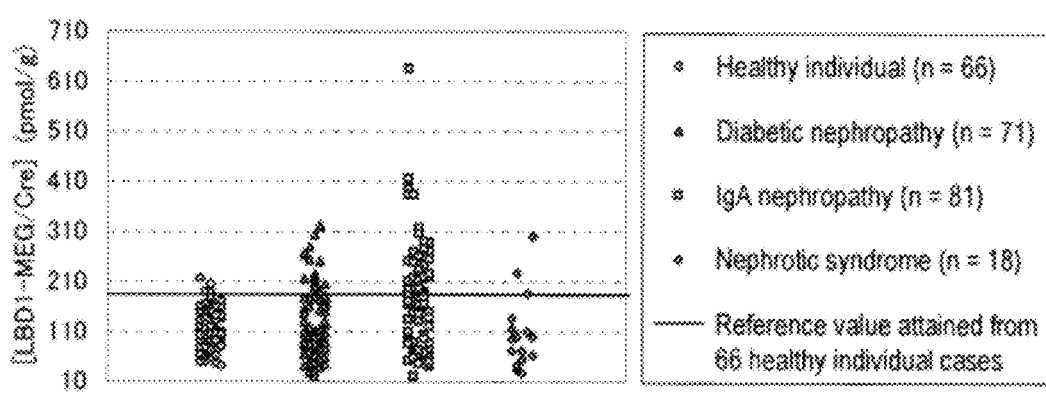
FIG. 5 shows the results of measurement of the amount of human megalin comprising an ectodomain excreted into the urine (creatinine correction value) in cases of type II diabetic nephropathy (71 cases), IgA nephropathy (81 cases), and nephrotic syndrome (18 cases).
Figure 6:
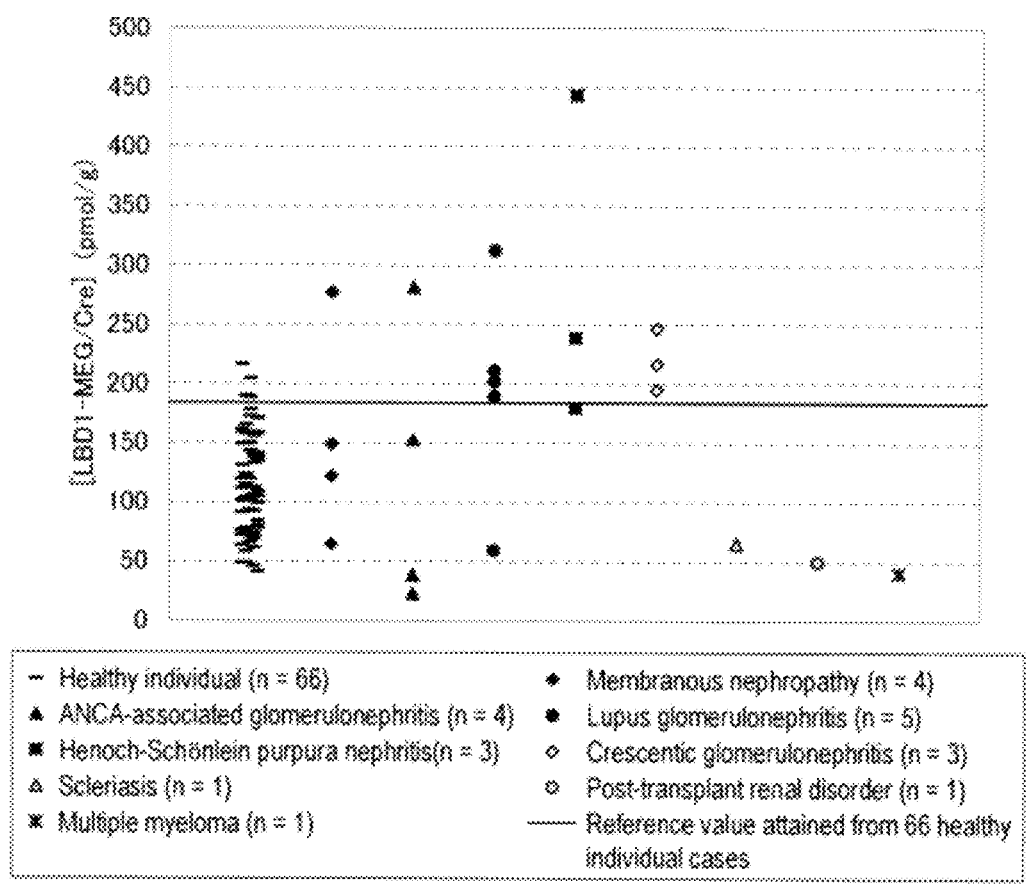
FIG. 6 shows the results of measurement of the amount of human megalin comprising an ectodomain excreted into the urine (creatinine correction value) in several other nephropathy cases.
Figure 7:
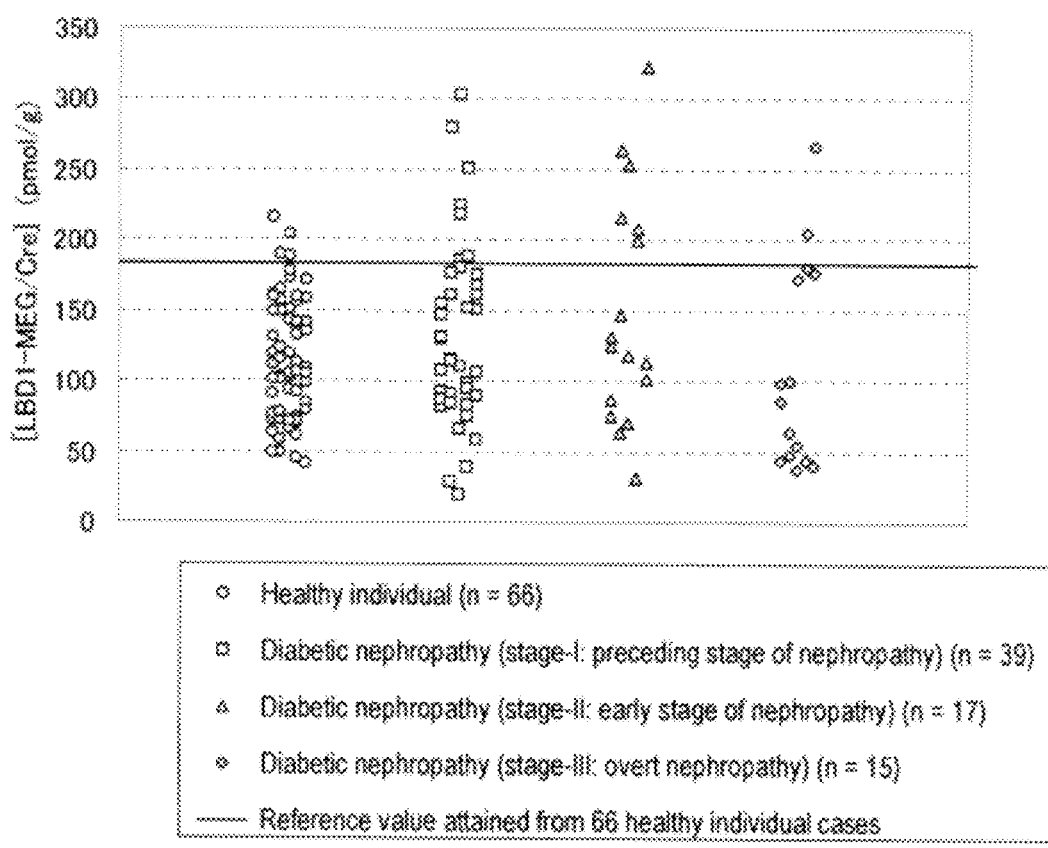
FIG. 7 shows the results of measurement of the amount of human megalin comprising an ectodomain excreted into the urine (creatinine correction value) in cases of type II diabetic nephropathy (71 cases) classified in accordance with the degree of albuminuria (classification based on severity of disorder) in accordance with staging of diabetic nephropathy.
Figure 8:
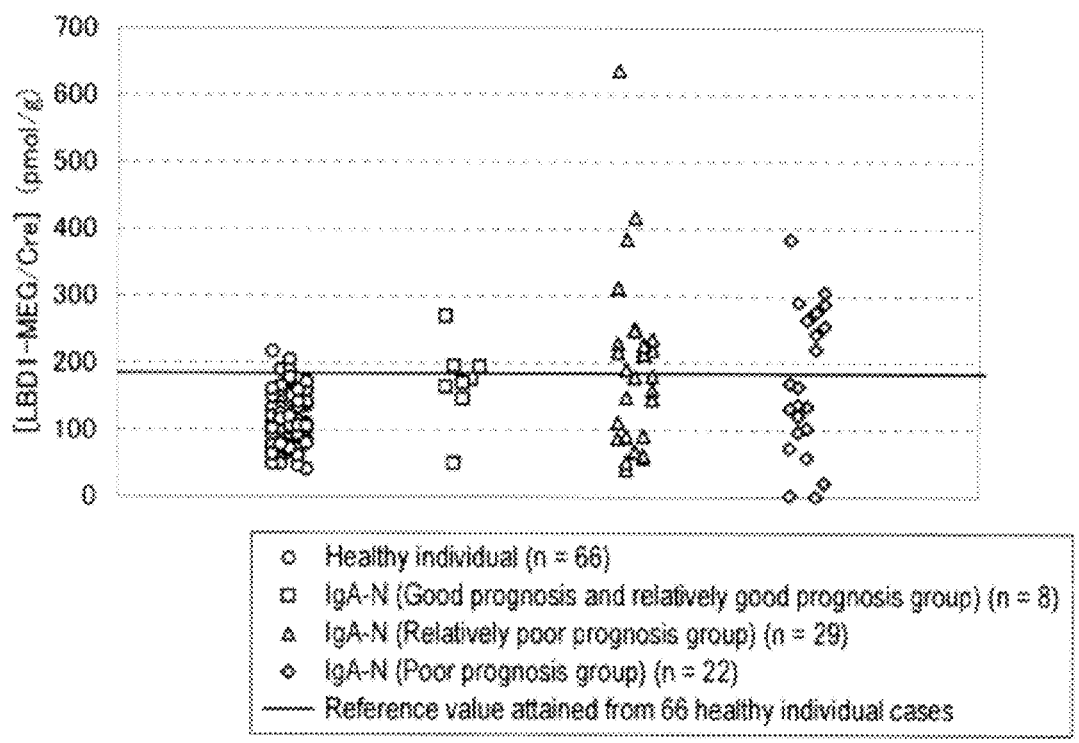
FIG. 8 shows the results of measurement of the amount of human megalin comprising an ectodomain excreted into the urine (creatinine correction value) in cases of IgA nephropathy (59 cases) based on histological classification of prognosis (prognosis achieved by histological classification of renal biopsies).
Figure 9:
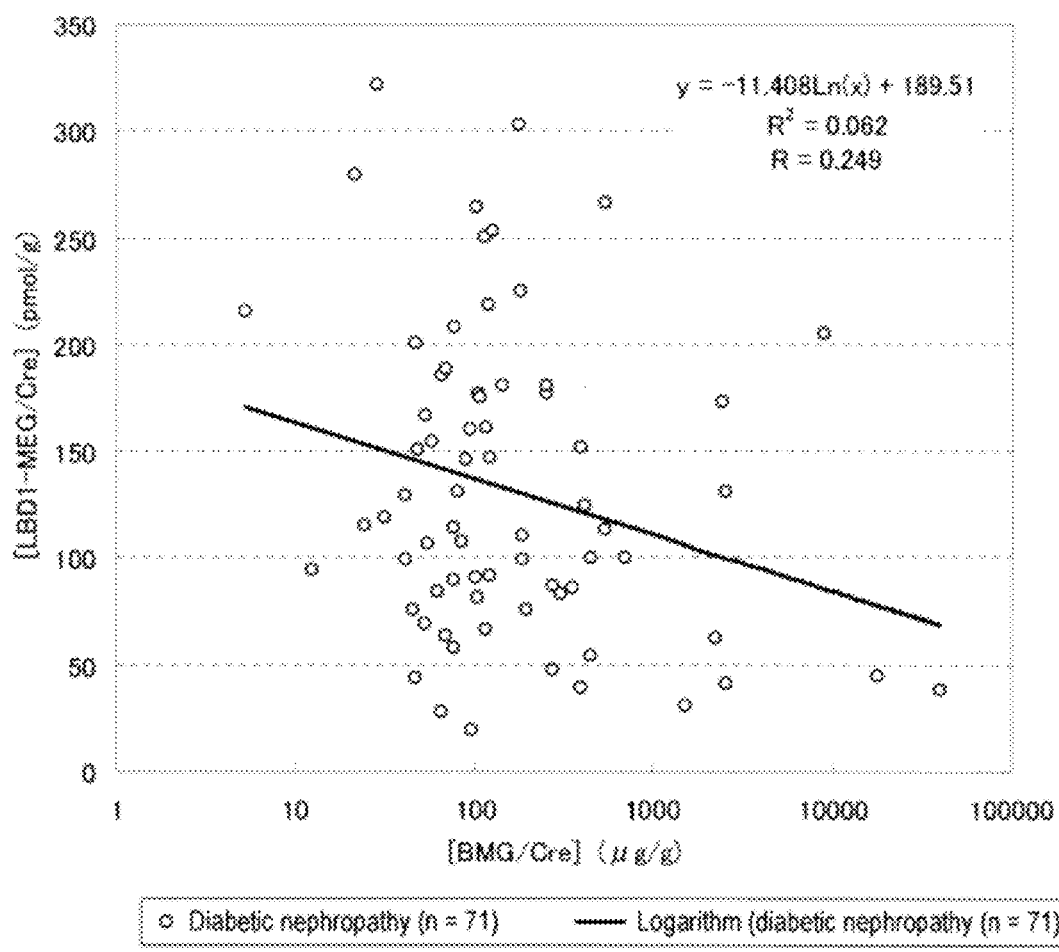
FIG. 9 shows the correlation between the 132-microglobulin concentration in urine and the amount of human megalin comprising an ectodomain excreted into the urine (creatinine correction value) in cases of type II diabetic nephropathy (71 cases).

Measurement of the Amount of Human Megalin Comprising Ectodomain Excreted into the Urine with the Use of a Ligand Capable of Binding to a Human Megalin Ectodomain Fragment Lacking an Endodomain The amount of human megalin comprising an ectodomain excreted into the urine was measured with the use of an anti-human megalin ectodomain fragment monoclonal antibody. The anti-human megalin ectodomain fragment monoclonal antibody is a mouse monoclonal antibody that recognizes an epitope located in a domain (LBD1) consisting of amino acids 26 to 314 of the amino acid sequence as shown in SEQ ID NO: 2. Measurement and evaluation were carried out with the use of the anti-human megalin LBD1 monoclonal antibody A and the anti-human megalin LBD1 monoclonal antibody B each recognizing a different epitope in LBD1. Human megalin comprising an ectodomain in the urine was measured using a microtiter plate on which the anti-human megalin LBD1 monoclonal antibody A had been immobilized and the ALP-labeled anti-human megalin LBD1 monoclonal antibody B. At the outset, 90 µl of primitive urine was mixed with 10 µl of a solution comprising 2 M Tris-HCl, 0.2 M EDTA, and 10% (vol/vol) Triton X-100 (pH 8.0), and 100 µl of the resulting mixture was applied to wells of the microtiter plate on which the anti-human megalin LBD1 monoclonal antibody A had been immobilized (FluoroNunc™ Module F16 Black-Maxisorp™ Surface plate, manufactured by Nalge Nunc International). The resultant was allowed to stand at 37° C. for 1 hour, the urine sample solution that had been applied to the wells was removed via decantation, a wash solution was applied to the wells of the microtiter plate at 200 µl/well, and the wash solution was removed via decantation, followed by washing. The process of washing was carried out three times in total. Thereafter, the solution of the ALP-labeled anti-human megalin LBD1 monoclonal antibody B (0.5 ng/ml) was applied at 100 µl/well. The ALP-labeled anti-human megalin LBD1 monoclonal antibody B was prepared in a diluent for labeled antibodies. The resultant was allowed to stand at 37° C. for 1 hour, the ALP-labeled antibody solution that had been applied to the wells was removed via decantation, a wash solution was applied to the wells of the microtiter plate at 200 µl/well, and the wash solution was removed via decantation, followed by washing. The process of washing was carried out four times in total. Thereafter, an assay buffer was applied to wells of the microtiter plate at 200 µl/well, and the assay buffer was removed via decantation, followed by washing. The process of washing was carried out twice in total. Subsequently, CDP-Star (registered trademark) chemiluminescent substrate for alkaline phosphatase ready-to-use (0.4 mM) with Emerald-II™ enhancer (ELISA-Light™ System, manufactured by Applied Biosystems) was applied to the wells as a substrate solution for ALP enzyme reaction at 100 µl/well, and the resultant was allowed to stand at 37° C. for 30 minutes while shielded from light. Immediately thereafter, the accumulated emission intensity of the wells for 1 second was measured, and the resulting value was designated as an indicator for measurement and evaluation of concentration of human megalin comprising an ectodomain in urine. The chemiluminescence intensity was measured using the Microplate Luminometer Centro LB960 and MicroWin2000 software (manufactured by Berthold). As the reference sample for the calibration curve, native human megalin extracted from the kidney was used. The results of actual clinical measurement of concentration of human megalin comprising an ectodomain in urine are shown in FIG. 5 and FIG. 6. Backgrounds of patients subjected to measurement, patients with type II diabetic nephropathy (71 cases), patients with IgA nephropathy (81 cases), and patients with nephrotic syndrome (18 cases), are shown in Table 1. As a result, the amount of human megalin comprising an ectodomain excreted into the urine was found to have increased significantly in patients with renal diseases and potential patients of renal diseases, compared with healthy individuals (FIGS. 5 and 6). The amount of megalin excreted into the urine was evaluated with the use of the creatinine correction value determined by dividing the megalin concentration in urine by the creatinine concentration in urine and correcting the concentration. Example 4 demonstrates that concentration of human megalin comprising an ectodomain in urine can be specifically measured and evaluated, and the amount of human megalin comprising an ectodomain excreted into the urine increases in accordance with the severity of diabetic nephropathy or prognostic classification of IgA nephropathy (FIGS. 7 and 8). Thus, measurement thereof was considered to be effective for recognition of pathological conditions and diagnosis of nephropathy. Backgrounds of patients with type II diabetic nephropathy (71 cases) and IgA nephropathy (81 cases) in accordance with the severity of pathological conditions are shown in Table 2 and Table 3. While $\beta$2-microglobulin is a blood-derived protein, $\beta$2-microglobulin generally permeates through the glomerular filtration slit, and it is reabsorbed by the proximal tubular epithelial cell mediated by megalin. The increased amount of $\beta$2-microglobulin excreted into the urine is considered to result from dysfunction of megalin-mediated reabsorption in the proximal tubule. The amount of human megalin comprising an ectodomain excreted into the urine is considered to be useful for evaluation of the megalin reabsorption capacity in the kidney. The decreased amount of human megalin comprising an ectodomain excreted into the urine can be considered to result from quenching of the megalin expression in the renal tissue. Accordingly, the lowered megalin-mediated reabsorption capacity in the kidney is considered to lead to the increased amount of $\beta$2-microglobulin excreted into the urine (FIG. 9). In contrast, the increased amount of human megalin comprising an ectodomain excreted into the urine means excessively elevated reabsorption. As a result of excessively elevated reabsorption, compensatory increase is considered to occur in the amount of human megalin comprising an ectodomain excreted into the urine. At the phase of compensation in which the increased amount of human megalin comprising an ectodomain excreted into the urine, the amount of $\beta$2-microglobulin excreted into the urine is maintained at a normal level in accordance with the state of excessively elevated reabsorption (FIG. 9), and whether or not stress is applied to the kidney can be evaluated by measuring concentration of human megalin comprising an ectodomain in urine. Accordingly, concentration of human megalin comprising an ectodomaine in urine is considered to be an effective indicator leading to early diagnosis and treatment (FIG. 9).

Example 5

Measurement of the Amount of Full-Length Human Megalin Excreted into the Urine With the use of the anti-human megalin ectodomain fragment monoclonal antibody and the anti-human megalin endodomain fragment monoclonal antibody, the amount of full-length human megalin excreted into the urine was measured.

The anti-human megalin ectodomain fragment monoclonal antibody is a mouse monoclonal antibody that recognizes an epitope located in a domain consisting of amino acids 26 to 314 of the amino acid sequence as shown in SEQ ID NO: 2 (i.e., the LBD1 domain). The anti-human megalin endodomain fragment monoclonal antibody is a mouse monoclonal antibody that recognizes an epitope located in a domain (Ctail) consisting of amino acids 4447 to 4655 of the amino acid sequence as shown in SEQ ID NO: 2.

Figure 10:
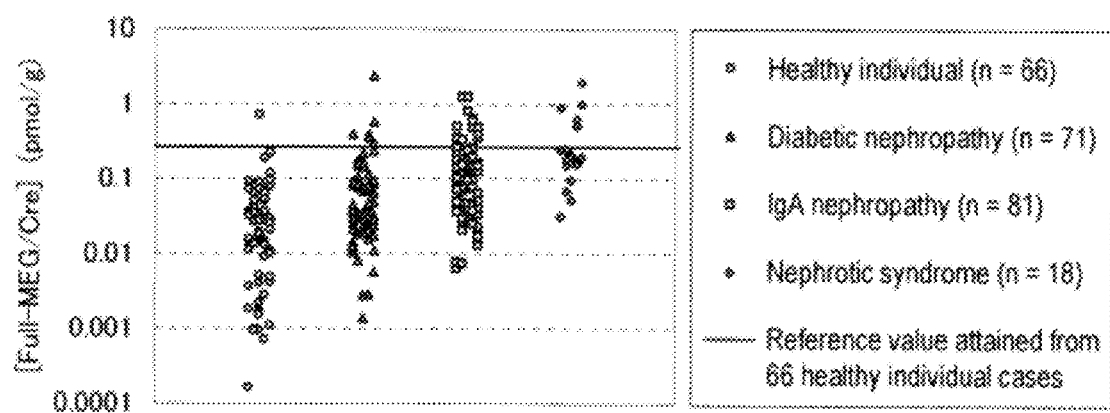
FIG. 10 shows the results of measurement of the amount of full-length human megalin excreted into the urine (creatinine correction value) in cases of type II diabetic nephropathy (71 cases), IgA nephropathy (81 cases), and nephrotic syndrome (18 cases).
Figure 11:
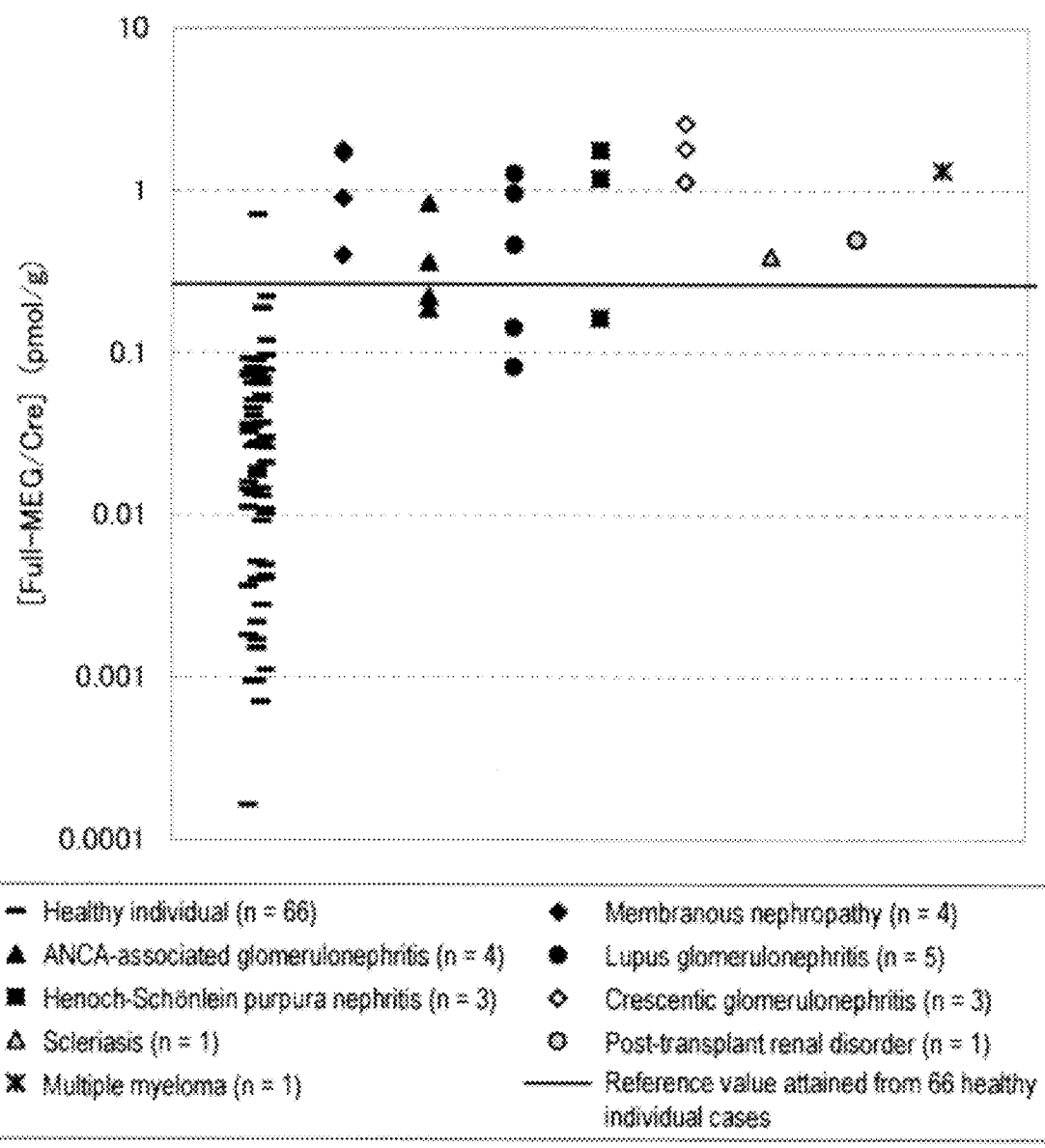
FIG. 11 shows the results of measurement of the amount of full-length human megalin excreted into the urine (creatinine correction value) in several other nephropathy cases.

With the use of a microtiter plate on which the anti-human megalin LBD1 monoclonal antibody had been immobilized and the alkaline phosphatage (hereafter abbreviated as "ALP")-labeled anti-human megalin Ctail monoclonal antibody, the amount of full-length human megalin in urine was measured. At the outset, 90 µl of primitive urine was mixed with 10 µl of a solution 2 M Tris-HCl, 0.2 M EDTA, and 10% (vol/vol) Triton X-100 (pH 8.0), and 100 µl of the resulting mixture was applied to wells of the microtiter plate on which the anti-human megalin LBD1 monoclonal antibodies had been immobilized (FluoroNunc™ Module F16 Black-Maxisorp™ Surface plate, manufactured by Nalge Nunc International). The resultant was allowed to stand at 37° C. for 1 hour, the urine sample solution that had been applied to the wells was removed via decantation, a wash solution was applied to the wells of the microtiter plate at 200 µl/well, and the wash solution was removed via decantation, followed by washing. The process of washing was carried out three times in total. Thereafter, the solution of the ALP-labeled anti-human megalin Ctail monoclonal antibody (0.5 ng/ml) was applied at 100 µl/well. The ALP-labeled anti-human megalin Ctail monoclonal antibody was prepared in a diluent for labeled antibodies. The resultant was allowed to stand at 37° C. for 1 hour, the ALP-labeled antibody solution that had been applied to the wells was removed via decantation, a wash solution was applied to the wells of the microtiter plate at 200 µl/well, and the wash solution was removed via decantation, followed by washing. The process of washing was carried out four times in total. Thereafter, an assay buffer was applied to wells of the microtiter plate at 200 µl/well, and the assay buffer was removed via decantation, followed by washing. The process of washing was carried out twice in total. Subsequently, CDP-Star (registered trademark) chemiluminescent substrate for alkaline phosphatase ready-to-use (0.4 mM) with Emerald-II™ enhancer (ELISA-Light™ System, manufactured by Applied Biosystems) was applied to the wells as a substrate solution for ALP enzyme reaction at 100 µl/well, and the resultant was allowed to stand at 37° C. for 30 minutes while shielded from light. Immediately thereafter, the accumulated emission intensity of the wells for 1 second was measured, and the resulting value was designated as an indicator for measurement and evaluation of full-length human megalin in urine. The chemiluminescence intensity was measured using the Microplate Luminometer Centro LB960 and MicroWin2000 software (manufactured by Berthold). As the reference sample for the calibration curve, native human megalin extracted from the kidney was used. The results of actual clinical measurement of human megalin in urine are shown in FIG. 10 and FIG. 11. Backgrounds of patients subjected to measurement, patients with type II diabetic nephropathy (71 cases), patients with IgA nephropathy (81 cases), and patients with nephrotic syndrome (18 cases), are shown in Table 1. As a result, excretion of full-length human megalin into the urine was observed (FIGS. 10 and 11). The amount of megalin excreted into the urine was evaluated with the use of the creatinine correction value determined by dividing the megalin concentration in urine by the creatinine concentration in urine and correcting the concentration.

Example 6

Differential Evaluation of Human Megalin Endodomain Fragment in Urine

Figure 12:
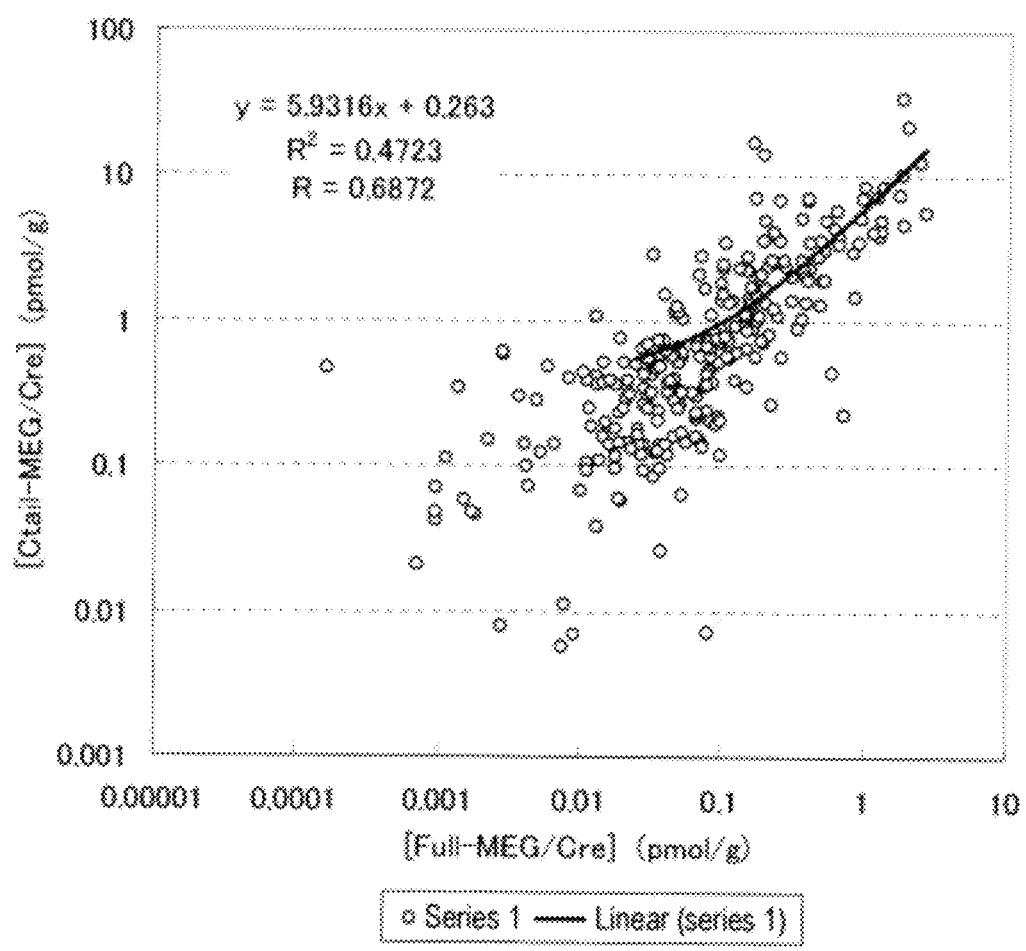
FIG. 12 shows the correlation between the concentration of full-length human megalin in urine and the concentration of human megalin comprising an endodomain in urine.
Figure 13:
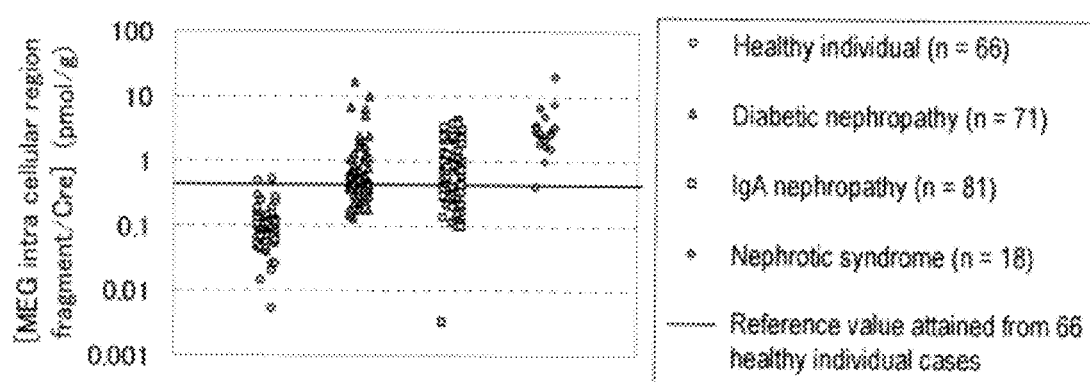
FIG. 13 shows the results of measurement of the amount of a human megalin endodomain fragment lacking an ectodomain excreted into the urine (creatinine correction value) in cases of type II diabetic nephropathy (71 cases), IgA nephropathy (81 cases), and nephrotic syndrome (18 cases).
Figure 14:
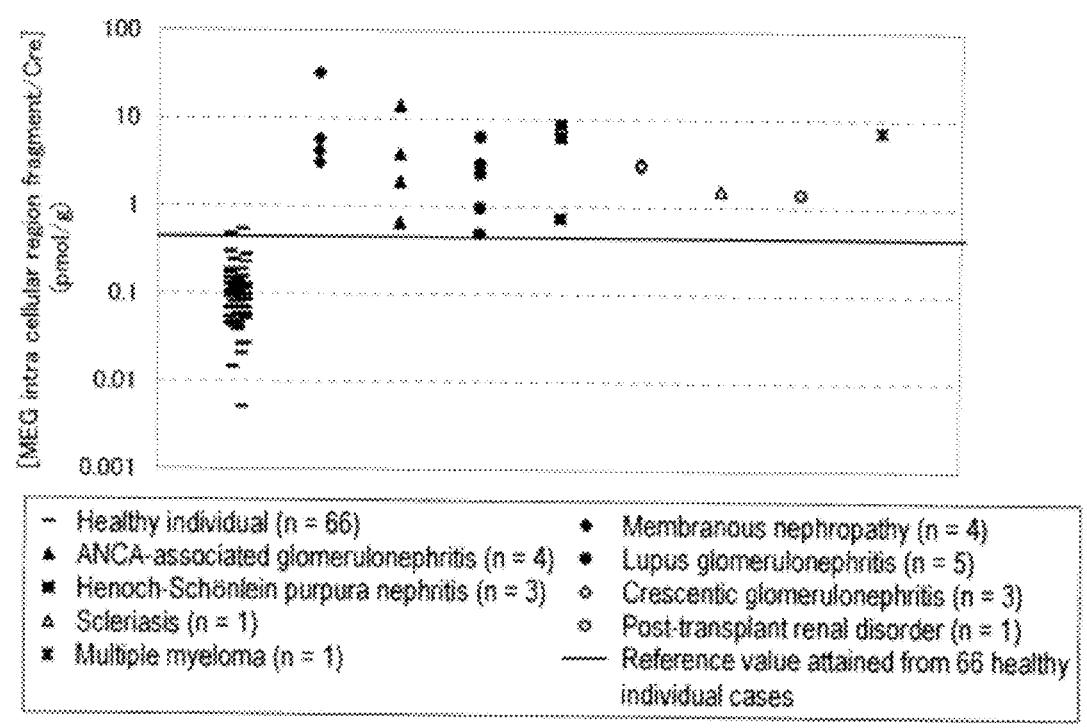
FIG. 14 shows the results of measurement of the amount of a human megalin endodomain fragment lacking an ectodomain excreted into the urine (creatinine correction value) in several other nephropathy cases.
Figure 15:
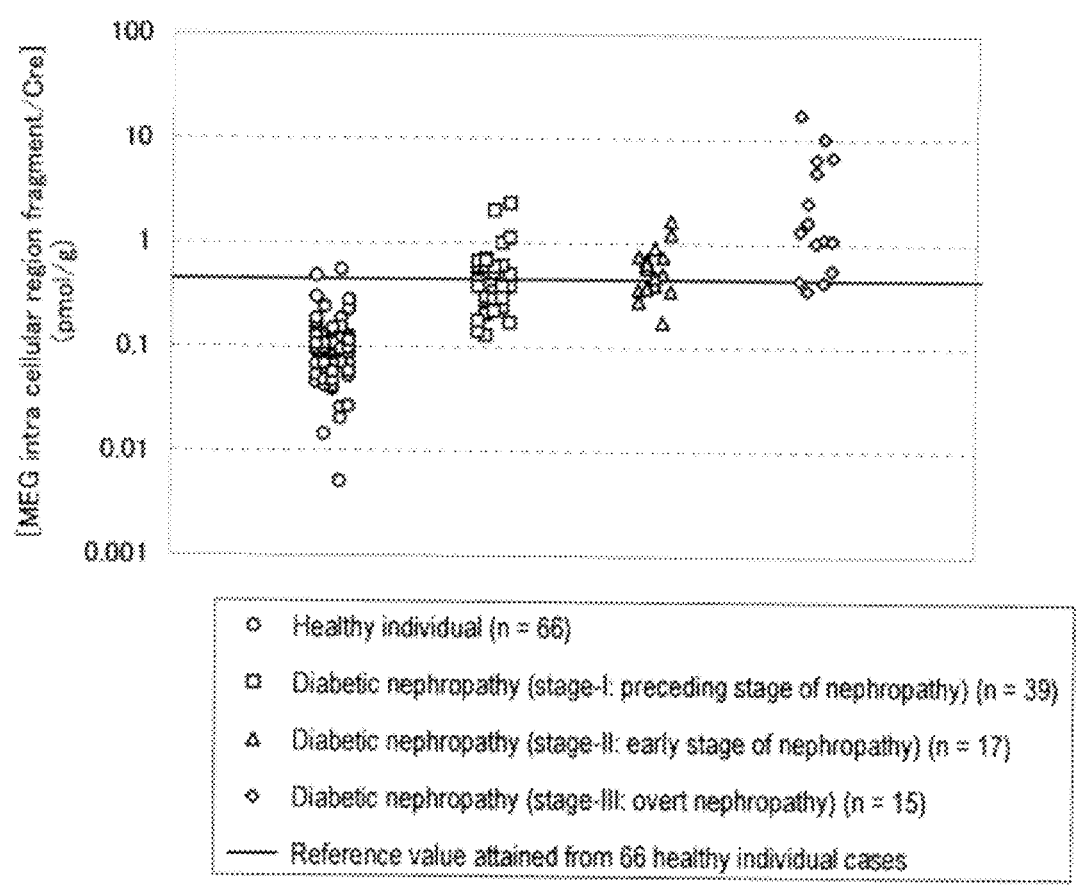
FIG. 15 shows the amount of a human megalin endodomain fragment lacking an ectodomain excreted into the urine (creatinine correction value) in cases of type II diabetic nephropathy (71 cases) classified in accordance with the degree of albuminuria (classification based on severity of disorder) in accordance with staging of diabetic nephropathy.
Figure 16:
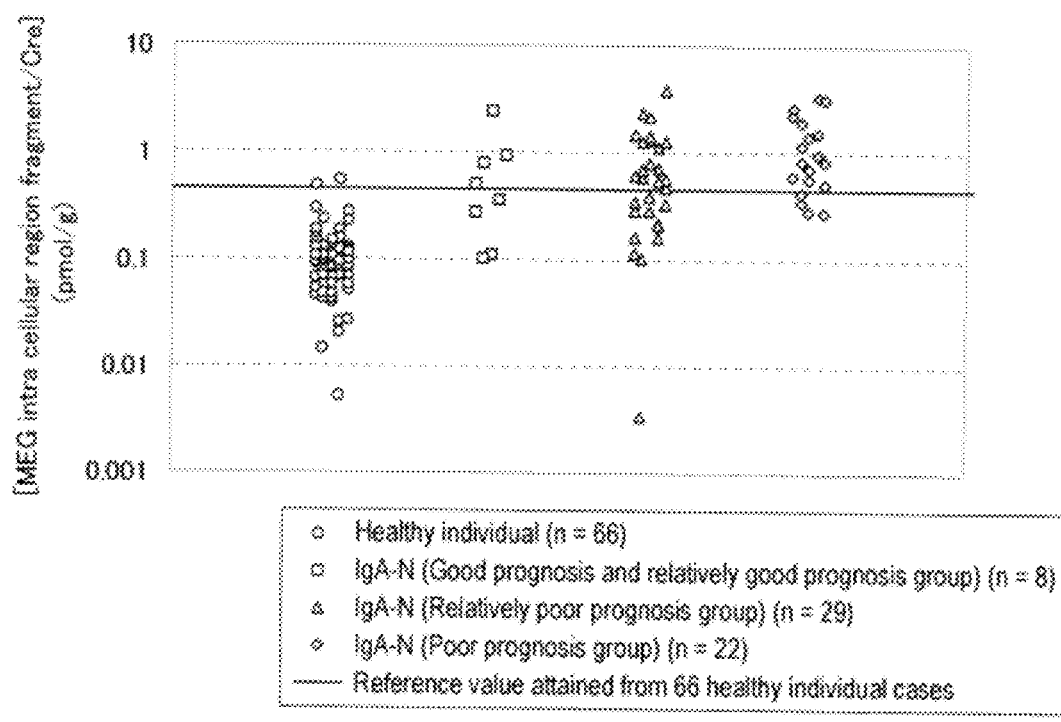
FIG. 16 shows the amount of a human megalin endodomain fragment lacking an ectodomain excreted into the urine (creatinine correction value) in cases of IgA nephropathy (59 cases) based on histological classification of prognosis (prognosis achieved by histological classification of renal biopsies).

The measured value for the human megalin comprising an endodomain obtained with the use of a ligand capable of binding to a human megalin endodomain fragment lacking an ectodomain in Example 1 reflects the sum of the measured value for full-length human megalin and that for the human megalin endodomain fragment. Thus, the value obtained by subtracting the measured value for full-length human megalin in urine obtained in Example 3 from the measured value for the human megalin comprising an endodomain in urine obtained in Example 1 is the true (net) value for the human megalin endodomain fragment in urine. Whether or not the value obtained by subtracting the measured value of Example 3 from that of Example 1 could be used as an indicator for diagnosis of a renal disease was evaluated. The amount of human megalin comprising an endodomain in urine measured in Example 1 was greater than that of full-length human megalin measured in Example 3, and there is a primary correlation therebetween (FIG. 12). It was thus found that the human megalin endodomain fragment lacking an ectodomain was excreted into the urine in accordance with a mechanism associated with excretion of full-length human megalin. Measurement of the amount of such human megalin endodomain fragment lacking an ectodomain excreted into the urine was considered to be effective for recognition of pathological conditions and diagnosis of nephropathy (FIGS. 13 to 16). Specifically, the increased amount of a human megalin endodomain fragment lacking an ectodomain excreted into the urine (the true value) was observed in accordance with the severity of type II diabetic nephropathy or prognostic classification of IgA nephropathy. Backgrounds of patients subjected to measurement, patients with type II diabetic nephropathy (71 cases), IgA nephropathy (81 cases), and nephrotic syndrome (18 cases), are shown in Table 1. Backgrounds of patients with type II diabetic nephropathy (71 cases) and IgA nephropathy (81 cases) in accordance with the severity of pathological conditions are shown in Table 2 and Table 3.

Example 7

Differential Evaluation of Human Megalin Ectodomain Fragment in Urine

Figure 17:
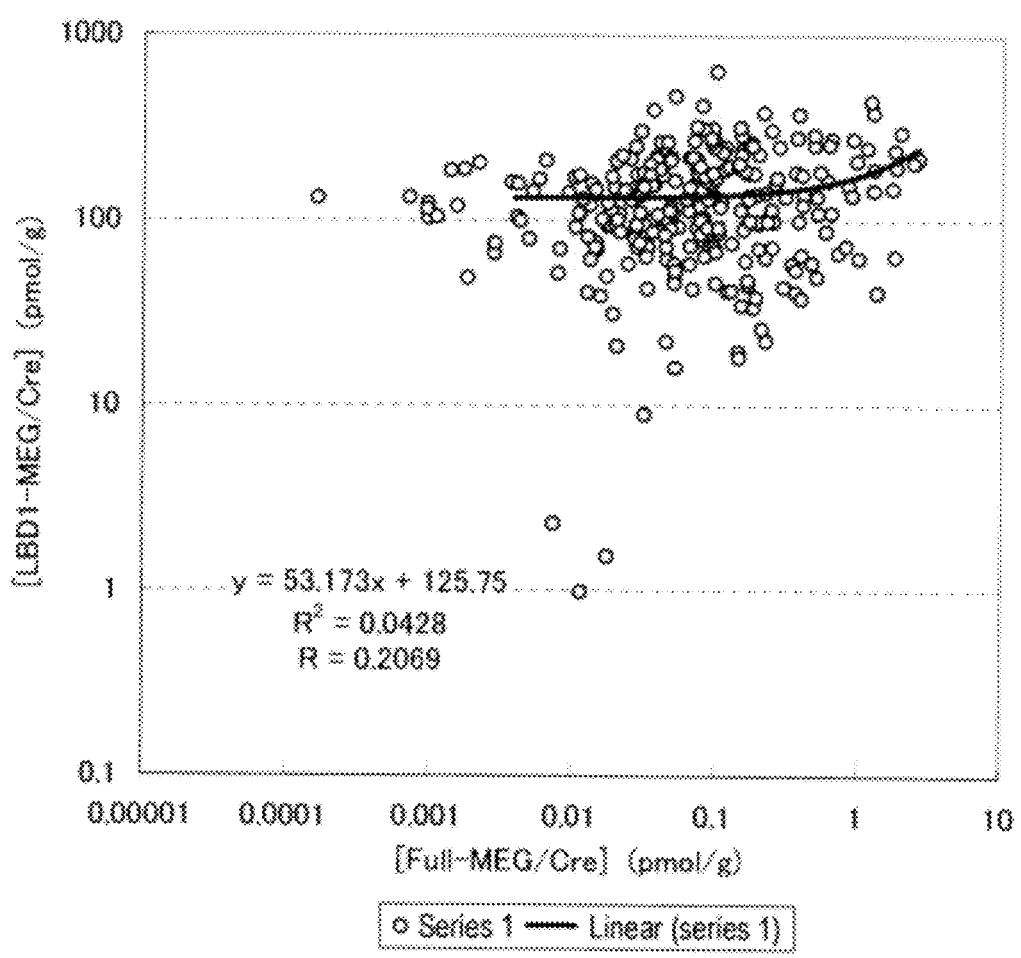
FIG. 17 shows the correlation between the concentration of full-length human megalin in urine and the concentration of human megalin comprising an ectodomain in urine.
Figure 18:
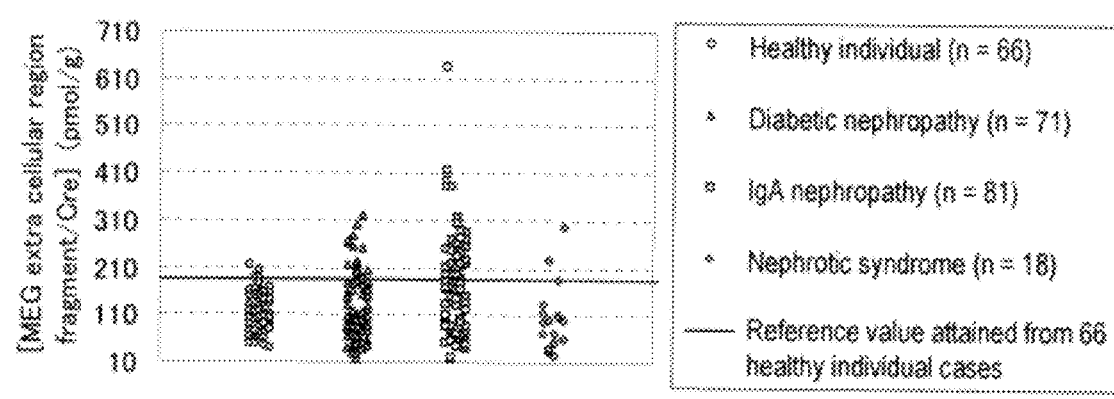
FIG. 18 shows the results of measurement of the amount of a human megalin ectodomain fragment lacking an endodomain excreted into the urine (creatinine correction value) in cases of type II diabetic nephropathy (71 cases), IgA nephropathy (81 cases), and nephrotic syndrome (18 cases).
Figure 19:
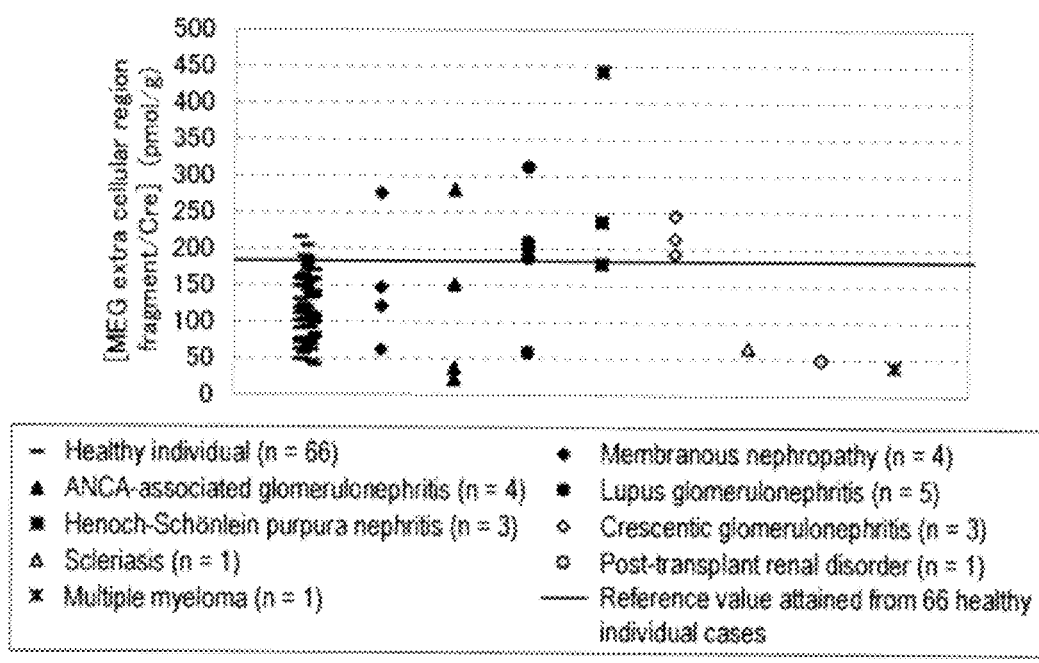
FIG. 19 shows the results of measurement of the amount of a human megalin ectodomain fragment lacking an endodomain excreted into the urine (creatinine correction value) in several other nephropathy cases.
Figure 20:
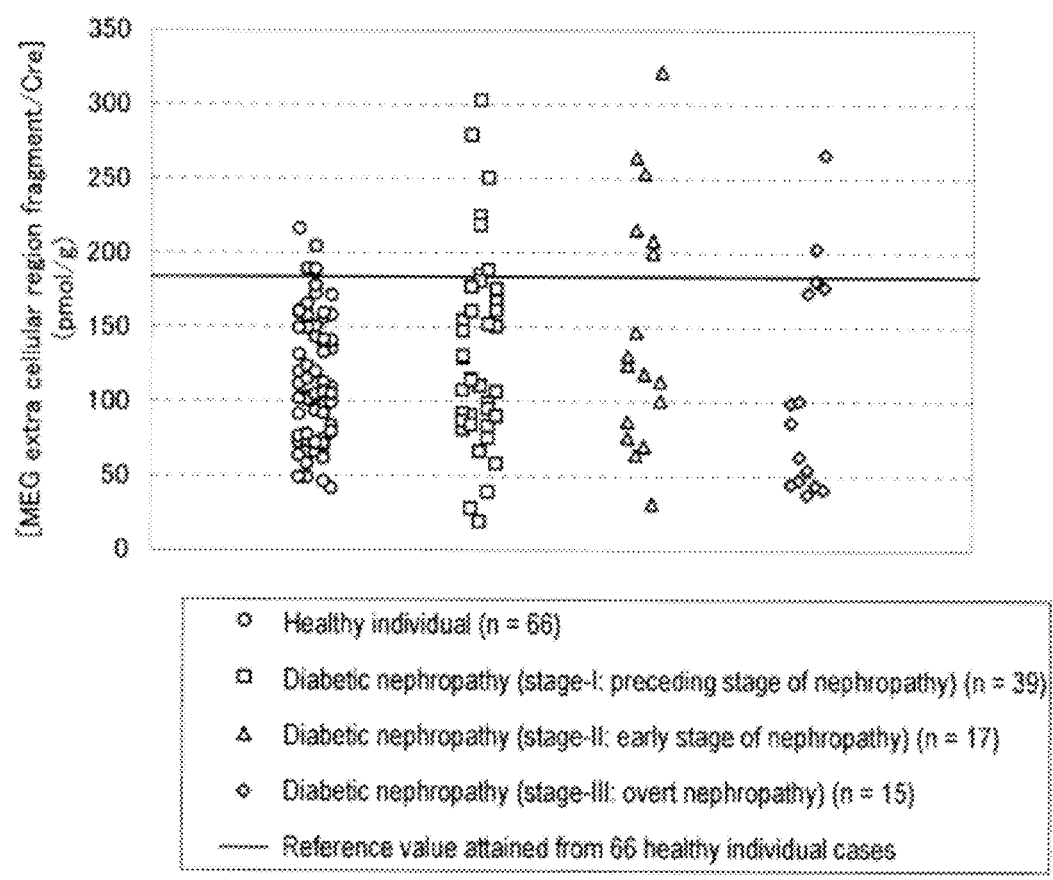
FIG. 20 shows the amount of a human megalin ectodomain fragment lacking an endodomain excreted into the urine (creatinine correction value) in cases of type II diabetic nephropathy (71 cases) classified in accordance with the degree of albuminuria (classification based on severity of disorder) in accordance with staging of diabetic nephropathy.
Figure 21:
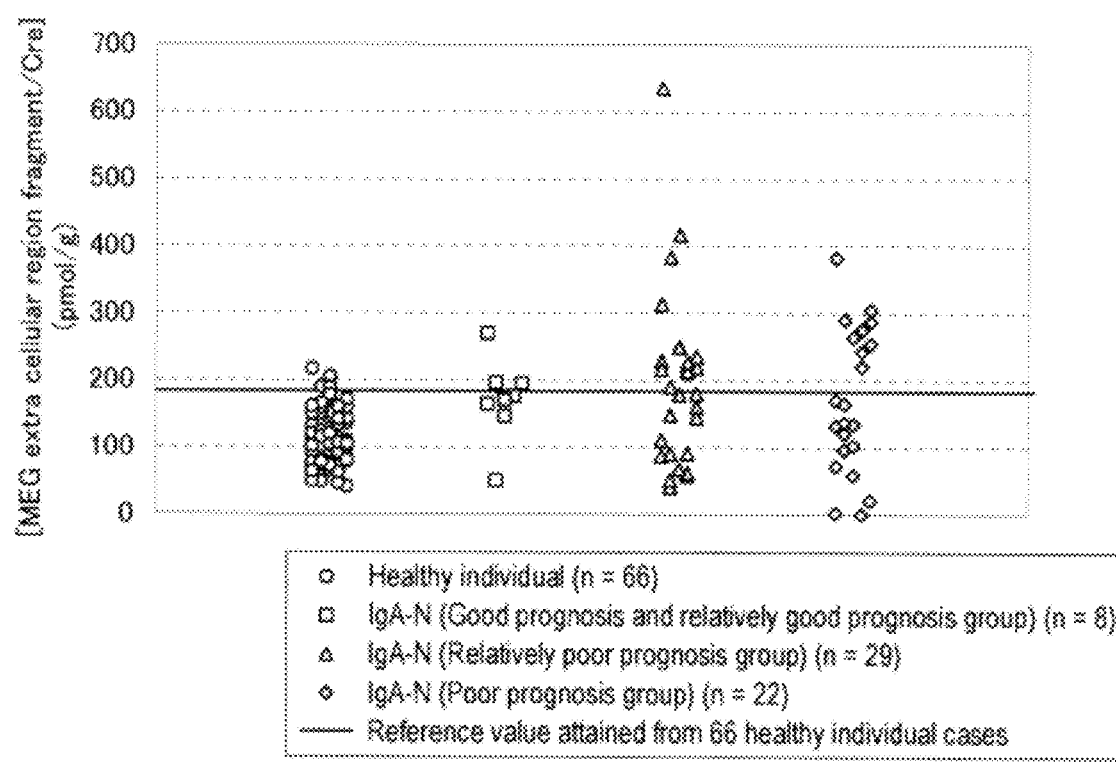
FIG. 21 shows the amount of a human megalin ectodomain fragment lacking an endodomain excreted into the urine (creatinine correction value) in cases of IgA nephropathy (59 cases) based on histological classification of prognosis (prognosis achieved by histological classification of renal biopsies).

The measured value for the human megalin comprising an ectodomain obtained with the use of a ligand capable of binding to a human megalin ectodomain fragment lacking an endodomain in Example 2 reflects the sum of the measured value for full-length human megalin and that for the human megalin ectodomain fragment. Thus, the value obtained by subtracting the measured value for full-length human megalin in urine obtained in Example 3 from the measured value for the human megalin comprising an ectodomain in urine obtained in Example 2 is the true (net) value for the human megalin ectodomain fragment in urine. Whether or not the value obtained by subtracting the measured value of Example 3 from that of Example 2 could be used as an indicator for diagnosis of a renal disease was evaluated. The amount of human megalin comprising an ectodomain in urine measured in Example 2 was greater than that of full-length human megalin measured in Example 3, and there is no correlation therebetween (FIG. 17). It was thus found that a large amount of the human megalin ectodomain fragment lacking an endodomain was excreted into the urine in accordance with a mechanism different from excretion of full-length human megalin. Measurement of the amount of such human megalin ectodomain fragment lacking an endodomain excreted into the urine was considered to be effective for recognition of pathological conditions and diagnosis of nephropathy (FIGS. 18 to 21). Backgrounds of patients subjected to measurement, patients with type II diabetic nephropathy (71 cases), IgA nephropathy (81 cases), and nephrotic syndrome (18 cases) are shown in Table 1. Backgrounds of patients with type II diabetic nephropathy (71 cases) and IgA nephropathy (81 cases) in accordance with the severity of pathological conditions, are shown in Table 2 and Table 3.

All publications, patents, and patent applications cited herein are incorporated herein by reference in their entirety.

INDUSTRIAL APPLICABILITY

The present invention enables measurement of the amount of human megalin excreted into the urine and differential evaluation of dynamics of three types of human megalins excreted into the urine: i.e., a human megalin ectodomain fragment; a human megalin endodomain fragment; and full-length human megalin. Evaluation of the amount of human megalin excreted into the urine and the dynamics of excretion found by the present invention enables recognition of pathological conditions of a renal disease, and, in particular, tubular dysfunctions. Accordingly, use of human megalin in urine as a diagnostic marker for a renal disease is effective for prognostic prediction of a renal disease and accurate and early evaluation of the degree of disorder (progression of pathological conditions). Thus, such use is considered to be useful from the viewpoint of preventive treatment at an earlier stage.

The invention claimed is:

1. A method for treating a subject suffering from a renal disease, comprising:
   (i) comparing an amount of human megalin ectodomain fragment measured in a urine sample of the subject to that of healthy individuals; and
   (ii) directing treatment of the subject pursuant to a prognosis based on said comparing, wherein
      (A) a higher amount of human megalin ectodomain fragment in the urine sample indicates a poor prognosis and
      (B) the renal disease is selected from the group consisting of diabetic nephropathy, IgA nephropathy, nephritic syndrome, lupus glomerulonephritis, Henoch-Schonlein purpura nephritis, crescentic glomerulonephritis.

2. A method for treating a subject at risk of advancement of renal disease, comprising:
   (i) determining that the subject's excretion level in urine for human megalin ectodomain fragment exceeds normal levels of excretion for said fragment, such that the subject is identified as having a high risk of renal disease advancement; and, on the basis of such identification,
   (ii) causing the subject to undergo preventive treatment;
   wherein the renal disease-associated with tubular dysfunction is selected from the group consisting of diabetic nephropathy, IgA nephropathy, nephritic syndrome, lupus glomerulonephritis, Henoch-Schonlein purpura nephritis, crescentic glomerulonephritis.

3. The method for detecting a renal disease according to claim 1, wherein the human megalin ectodomain fragment in the urine sample has an amino acid sequence corresponding to amino acids 26 to 4361, amino acids 26 to 314, or amino acids 4362-4437 of SEQ ID NO. 2.

4. The method for detecting a renal disease according to claim 2, wherein the human megalin ectodomain fragment in the urine sample has an amino acid sequence corresponding to amino acids 26 to 4361, amino acids 26 to 314, or amino acids 4362-4437 of SEQ ID NO. 2.

* * * * *

SEQUENCE LISTING

```
<160> NUMBER OF SEQ ID NOS: 2

<210> SEQ ID NO 1
<211> LENGTH: 13968
<212> TYPE: DNA
<213> ORGANISM: Homo sapiens

<400> SEQUENCE: 1
atggatcgcg ggccggcagc agtggcgtgc acgctgctcc tggctctcgt cgcctgccta      60
gcgccggcca gtggccaaga atgtgacagt gcgcattttc gctgtggaag tgggcattgc     120
atccctgcag actggaggtg tgatgggacc aaagactgtt cagatgacgc ggatgaaatt     180
ggctgcgctg ttgtgacctg ccagcagggc tatttcaagt gccagagtga gggacaatgc     240
atccccagct cctgggtgtg tgaccaagat caagactgtg atgatggctc agatgaacgt     300
caagattgct cacaaagtac atgctcaagt catcagataa catgctccaa tggtcagtgt     360
atcccaagtg aatacaggtg cgaccacgtc agagactgcc ccgatggagc tgatgagaat     420
gactgccagt acccaacatg tgagcagctt acttgtgaca atggggcctg ctataacacc     480
agtcagaagt gtgattggaa agttgattgc agggactcct cagatgaaat caactgcact     540
gagatatgct tgcacaatga gttttcatgt ggcaatggag agtgtatccc tcgtgcttat     600
gtctgtgacc atgacaatga ttgccaagac ggcagtgatg aacatgcttg caactatccg     660
acctgcggtg gttaccagtt cacttgcccc agtggccgat gcatttatca aaactgggtt     720
tgtgatggag aagatgactg taaagataat ggagatgaag atggatgtga aagcggtcct     780
catgatgttc ataaatgttc cccaagagaa tggtcttgcc cagagtcggg acgatgcatc     840
tccatttata aagtttgtga tgggattta gattgcccag aagagaaga tgaaaacaac     900 actagtaccg gaaaatactg tagtatgact ctgtgctctg ccttgaactg ccagtaccag     960
tgccatgaga cgccgtatgg aggagcgtgt ttttgtcccc caggttatat catcaaccac    1020
aatgacagcc gtacctgtgt tgagtttgat gattgccaga tatggggaat ttgtgaccag    1080
aagtgtgaaa gccgacctgg ccgtcacctg tgccactgtg aagaagggta tcttggag     1140 cgtggacagt attgcaaagc taatgattcc tttggcgagg cctccattat cttctccaat    1200
ggtcgggatt tgttaattgg tgatattcat ggaaggagct tccggatcct agtggagtct    1260
cagaatcgtg gagtggccgt gggtgtggct ttccactatc acctgcaaag agttttttgg    1320
acagacaccg tgcaaaataa ggtttttca gttgacatta atggtttaaa tatccaagag    1380
```

```
gttctcaatg tttctgttga aaccccagag aacctggctg tggactgggt taataataaa   1440
atctatctag tggaaaccaa ggtcaaccgc atagatatgg taaatttgga tggaagctat   1500
cgggttaccc ttataactga aaacttgggg catcctagag gaattgccgt ggacccaact   1560
gttggttatt tattttctc agattgggag agcctttctg gggaacctaa gctggaaagg    1620
gcattcatgg atggcagcaa ccgtaaagac ttggtgaaaa caaagctggg atggcctgct   1680
ggggtaactc tggatatgat atcgaagcgt gtttactggg ttgactctcg gtttgattac   1740
attgaaactg taacttatga tggaattcaa aggaagactg tagttcatgg aggctccctc   1800
attcctcatc cctttggagt aagcttattt gaaggtcagg tgttctttac agattggaca   1860
aagatggccg tgctgaaggc aaacaagttc acagagacca acccacaagt gtactaccag   1920
gcttccctga ggcccatgg agtgactgtt taccattccc tcagacagcc ctatgctacc    1980
aatccgtgta agataacaa tgggggctgt gagcaggtct gtgttctcag ccacagaaca    2040
gataatgatg gtttgggttt ccgttgcaag tgcacattcg gcttccaact ggatacagat   2100
gagcgccact gcattgctgt tcagaatttc ctcattttt catcccaagt tgctattcgt    2160
gggatcccgt tcaccttgtc tacccaggaa gatgtcatgg ttccagtttc ggggaatcct   2220
tctttctttg tcgggattga ttttgacgcc caggacagca ctatctttt ttcagatatg     2280 tcaaaacaca tgattttaa gcaaaagatt gatggcacag gaagagaaat tctcgcagct    2340
aacagggtgg aaaatgttga agtttggct tttgattgga tttcaaagaa tctctattgg     2400
acagactctc attacaagag tatcagtgtc atgaggctag ctgataaaac gagacgcaca   2460
gtagttcagt atttaaataa cccacggtcg gtggtagttc atccttttgc cgggtatcta   2520
ttcttcactg attggttccg tcctgctaaa attatgagag catggagtga cggatctcac   2580
ctcttgcctg taataaacac tactcttgga tggcccaatg gcttggccat cgattgggct   2640
gcttcacgat tgtactgggt agatgccatt tttgataaaa ttgagcacag caccttgat     2700 ggtttagaca gaagaagact gggccatata gagcagatga cacatccgtt tggacttgcc   2760
atctttggag agcatttatt ttttactgac tggagactgg gtgccattat tcgagtcagg   2820
aaagcagatg gtggagaaat gacagttatc cgaagtggca ttgcttacat actgcatttg   2880
aaatcgtatg atgtcaacat ccagactggt tctaacgcct gtaatcaacc cacgcatcct   2940
aacggtgact gcagccactt ctgcttcccg gtgccaaatt tccagcgagt gtgtgggtgc   3000
ccttatggaa tgaggctggc ttccaatcac ttgacatgcg aggggaccc aaccaatgaa    3060 ccacccacgg agcagtgtgg cttattttcc ttcccctgta aaaatggcag atgtgtgccc   3120
aattactatc tctgtgatgg agtcgatgat tgtcatgata acagtgatga gcaactatgt   3180
ggcacactta ataatacctg ttcatcttcg gcgttcacct gtggccatgg ggagtgcatt   3240
cctgcacact ggcgctgtga caaacgcaac gactgtgtgg atggcagtga tgagcacaac   3300
tgccccaccc acgcacctgc ttcctgcctt gacacccaat acacctgtga taatcaccag   3360
tgtatctcaa agaactgggt ctgtgacaca gacaatgatt gtggggatgg atctgatgaa   3420
aagaactgca attcgacaga gacatgccaa cctagtcagt ttaattgccc caatcatcga   3480
tgtattgacc tatcgtttgt ctgtgatggt gacaaggatt gtgttgatgg atctgatgag   3540
gttggttgtg tattaaactg tactgcttct caattcaagt gtgccagtgg ggataaatgt   3600
attggcgtca caaatcgttg tgatggtgtt tttgattgca gtgacaactc ggatgaagcg   3660
ggctgtccaa ccaggcctcc tggtatgtgc cactcagatg aatttcagtg ccaagaagat   3720
ggtatctgca tcccgaactt ctgggaatgt gatgggcatc cagactgcct ctatggatct   3780
```

```
gatgagcaca atgcctgtgt ccccaagact tgcccttcat catatttcca ctgtgacaac   3840
ggaaactgca tccacagggc atggctctgt gatcgggaca atgactgcgg ggatatgagt   3900
gatgagaagg actgccctac tcagccctt cgctgtccta gttggcaatg gcagtgtctt    3960
ggccataaca tctgtgtgaa tctgagtgta gtgtgtgatg catctttga ctgccccaat    4020 gggacagatg agtccccact ttgcaatggg aacagctgct cagatttcaa tggtggttgt   4080
actcacgagt gtgttcaaga gcccttggg gctaaatgcc tatgtccatt gggattctta    4140
cttgccaatg attctaagac ctgtgaagac atagatgaat gtgatattct aggctcttgt   4200
agccagcact gttacaatat gagaggttct ttccggtgct cgtgtgatac aggctacatg   4260
ttagaaagtg atgggaggac ttgcaaagtt acagcatctg agagtctgct gttacttgtg   4320
gcaagtcaga acaaaattat tgccgacagt gtcacctccc aggtccacaa tatctattca   4380
ttggtcgaga atggttctta cattgtagct gttgattttg attcaattag tggtcgtatc   4440
ttttggtctg atgcaactca gggtaaaacc tggagtgcgt ttcaaaatgg aacggacaga   4500
agagtggtat ttgacagtag catcatcttg actgaaacta ttgcaataga ttgggtaggt   4560
cgtaatcttt actggacaga ctatgctctg gaaacaattg aagtctccaa aattgatggg   4620
agccacagga ctgtgctgat tagtaaaaac ctaacaaatc caagaggact agcattagat   4680
cccagaatga atgagcatct actgttctgg tctgactggg gccaccaccc tcgcatcgag   4740
cgagccagca tggacggcag catgcgcact gtcattgtcc aggacaagat cttctggccc   4800
tgcggcttaa ctattgacta ccccaacaga ctgctctact tcatggactc ctatcttgat   4860
tacatggact tttgcgatta taatggacac catcggagac aggtgatagc cagtgatttg   4920
attatacggc acccctatgc cctaactctc tttgaagact ctgtgtactg gactgaccgt   4980
gctactcgtc gggttatgcg agccaacaag tggcatggag ggaaccagtc agttgtaatg   5040
tataatattc aatggcccct tgggattgtt gcggttcatc cttcgaaaca accaaattcc   5100
gtgaatccat gtgcctttc ccgctgcagc catctctgcc tgctttcctc acaggggcct    5160 cattttact cctgtgtttg tccttcagga tggagtctgt ctcctgatct cctgaattgc    5220
ttgagagatg atcaaccttt cttaataact gtaaggcaac atataatttt tggaatctcc   5280
cttaatcctg aggtgaagag caatgatgct atggtcccca tagcagggat acagaatggt   5340
ttagatgttg aatttgatga tgctgagcaa tacatctatt gggttgaaaa tccaggtgaa   5400
attcacagag tgaagacaga tggcaccaac aggacagtat ttgcttctat atctatggtg   5460
gggccttcta tgaacctggc cttagattgg atttcaagaa acctttattc taccaatcct   5520
agaactcagt caatcgaggt tttgacactc cacggagata tcagatacag aaaaacattg   5580
attgccaatg atgggacagc tcttggagtt ggcttccaa ttggcataac tgttgatcct    5640
gctcgtggga agctgtactg gtcagaccaa ggaactgaca gtggggttcc tgccaagatc   5700
gccagtgcta acatggatgg cacatctgtg aaaactctct ttactgggaa cctcgaacac   5760
ctggagtgtg tcactcttga catcgaagag cagaaactct actgggcagt cactggaaga   5820
ggagtgattg aaagaggaaa cgtggatgga acagatcgga tgatcctggt acaccagctt   5880
tcccacccct ggggaattgc agtccatgat tctttccttt attatactga tgaacagtat   5940
gaggtcattg aaagagttga taaggccact ggggccaaca aaatagtctt gagagataat   6000
gttccaaatc tgagggggtct tcaagtttat cacagacgca atgccgccga atcctcaaat   6060
ggctgtagca acaacatgaa tgcctgtcag cagatttgcc tgcctgtacc aggaggattg   6120
ttttcctgcg cctgtgccac tggatttaaa ctcaatcctg ataatcggtc ctgctctcca   6180
```

| | |
|---|---|
| tataactctt tcattgttgt ttcaatgctg tctgcaatca gaggctttag cttggaattg | 6240 |
| tcagatcatt cagaaaccat ggtgccggtg gcaggccaag gacgaaacgc actgcatgtg | 6300 |
| gatgtggatg tgtcctctgg ctttatttat tggtgtgatt ttagcagctc agtggcatct | 6360 |
| gataatgcga tccgtagaat taaaccagat ggatcttctc tgatgaacat tgtgacacat | 6420 |
| ggaataggag aaaatggagt ccggggtatt gcagtggatt gggtagcagg aaatctttat | 6480 |
| ttcaccaatg cctttgtttc tgaaacactg atagaagttc tgcggatcaa tactacttac | 6540 |
| cgccgtgttc ttcttaaagt cacagtggac atgcctaggc atattgttgt agatcccaag | 6600 |
| aacagatacc tcttctgggc tgactatggg cagagaccaa agattgagcg ttctttcctt | 6660 |
| gactgtacca atcgaacagt gcttgtgtca gagggcattg tcacaccacg ggcttggca | 6720 |
| gtggaccgaa gtgatggcta cgtttattgg gttgatgatt ctttagatat aattgcaagg | 6780 |
| attcgtatca atggagagaa ctctgaagtg attcgttatg gcagtcgtta cccaactcct | 6840 |
| tatggcatca ctgtttttga aaattctatc atatgggtag ataggaattt gaaaaagatc | 6900 |
| ttccaagcca gcaaggaacc agagaacaca gagccaccca cagtgataag agacaatatc | 6960 |
| aactggctaa gagatgtgac catctttgac aagcaagtcc agccccggtc accagcagag | 7020 |
| gtcaacaaca acccttgctt ggaaaacaat ggtgggtgct ctcatctctg ctttgctctg | 7080 |
| cctggattgc acaccccaaa atgtgactgt gcctttggga ccctgcaaag tgatggcaag | 7140 |
| aattgtgcca tttcaacaga aaatttcctc atctttgcct tgtctaattc cttgagaagc | 7200 |
| ttacacttgg accctgaaaa ccatagccca ccttttccaaa caataaatgt ggaaagaact | 7260 |
| gtcatgtctc tagactatga cagtgtaagt gatagaatct acttcacaca aaatttagcc | 7320 |
| tctggagttg gacagatttc ctatgccacc ctgtcttcag ggatccatac tccaactgtc | 7380 |
| attgcttcag gtatagggac tgctgatggc attgcctttg actggattac tagaagaatt | 7440 |
| tattacagtg actacctcaa ccagatgatt aattccatgg ctgaagatgg gtctaaccgc | 7500 |
| actgtgatag cccgcgttcc aaaaccaaga gcaattgtgt tagatccctg ccaagggtac | 7560 |
| ctgtactggg ctgactggga tacacatgcc aaaatcgaga gagccacatt gggaggaaac | 7620 |
| ttccgggtac ccattgtgaa cagcagtctg gtcatgccca gtgggctgac tctggactat | 7680 |
| gaagaggacc ttctctactg ggtggatgct agtctgcaga ggattgaacg cagcactctg | 7740 |
| acgggcgtgg atcgtgaagt cattgtcaat gcagccgttc atgcttttgg cttgactctc | 7800 |
| tatggccagt atatttactg gactgacttg tacacacaaa gaatttaccg agctaacaaa | 7860 |
| tatgacgggt caggtcagat tgcaatgacc acaaatttgc tctcccagcc cagggggaatc | 7920 |
| aacactgttg tgaagaacca gaaacaacag tgtaacaatc cttgtgaaca gtttaatggg | 7980 |
| ggctgcagcc atatctgtgc accaggtcca aatggtgccg agtgccagtg tccacatgag | 8040 |
| ggcaactggt atttggccaa caccaggaag cactgcattg tggacaatgg tgaacgatgt | 8100 |
| ggtgcatctt ccttcacctg ctccaatggg cgctgcatct cggaagagtg gaagtgtgat | 8160 |
| aatgacaacg actgtgggga tggcagtgat gagatggaaa gtgtctgtgc acttcacacc | 8220 |
| tgctcaccga cagccttcac ctgtgccaat ggcgatgtgt ccaatactc ttaccgctgt | 8280 |
| gattactaca atgactgtgg tgatggcagt gatgaggcag ggtgcctgtt cagggactgc | 8340 |
| aatgccacca cggagtttat gtgcaataac agaaggtgca tacctcgtga gtttatctgc | 8400 |
| aatggtgtag acaactgcca tgataataac acttcagatg agaaaaattg ccctgatcgc | 8460 |
| acttgccagt ctggatacac aaaatgtcat aattcaaata tttgtattcc tcgcgtttat | 8520 |
| ttgtgtgacg gagacaatga ctgtggagat aacagtgatg aaaaccctac ttattgcacc | 8580 |

```
actcacacat gcagcagcag tgagttccaa tgcgcatctg ggcgctgtat tcctcaacat    8640
tggtattgtg atcaagaaac agattgtttt gatgcctctg atgaacctgc ctcttgtggt    8700
cactctgagc gaacatgcct agctgatgag ttcaagtgtg atggtgggag gtgcatccca    8760
agcgaatgga tctgtgacgg tgataatgac tgtggggata tgagtgacga ggataaaagg    8820
caccagtgtc agaatcaaaa ctgctcggat tccgagtttc tctgtgtaaa tgacagacct    8880
ccggacagga ggtgcattcc ccagtcttgg gtctgtgatg gcgatgtgga ttgtactgac    8940
ggctacgatg agaatcagaa ttgcaccagg agaacttgct ctgaaaatga attcacctgt    9000
ggttacggac tgtgtatccc aaagatattc aggtgtgacc ggcacaatga ctgtggtgac    9060
tatagcgacg agaggggctg cttataccag acttgccaac agaatcagtt tacctgtcag    9120
aacgggcgct gcattagtaa aaccttcgtc tgtgatgagg ataatgactg tggagacgga    9180
tctgatgagc tgatgcacct gtgccacacc ccagaaccca cgtgtccacc tcacgagttc    9240
aagtgtgaca atgggcgctg catcgagatg atgaaactct gcaaccacct agatgactgt    9300
ttggacaaca gcgatgagaa aggctgtggc attaatgaat gccatgaccc ttcaatcagt    9360
ggctgcgatc acaactgcac agacaccttt accagtttct attgttcctg tcgtcctggt    9420
tacaagctca tgtctgacaa gcggacttgt gttgatattg atgaatgcac agagatgcct    9480
tttgtctgta gccagaagtg tgagaatgta ataggctcct acatctgtaa gtgtgcccca    9540
ggctacctcc gagaaccaga tggaaagacc tgccggcaaa acagtaacat cgaaccctat    9600 ctcatttta gcaaccgtta ctatttgaga aatttaacta tagatggcta ttttttactcc    9660 ctcatcttgg aaggactgga caatgttgtg gcattagatt ttgaccgagt agagaagaga    9720
ttgtattgga ttgatacaca gaggcaagtc attgagagaa tgtttctgaa taagacaaac    9780
aaggagacaa tcataaacca cagactacca gctgcagaaa gtctggctgt agactgggtt    9840
tccagaaagc tctactggtt ggatgcccgc ctggatggcc tctttgtctc tgacctcaat    9900
ggtggacacc gccgcatgct ggcccagcac tgtgtggatg ccaacaacac cttctgcttt    9960
gataatccca gaggacttgc ccttcaccct caatatgggt acctctactg ggcagactgg   10020
ggtcaccgcg catacattgg gagagtaggc atggatggaa ccaacaagtc tgtgataatc   10080
tccaccaagt tagagtggcc taatggcatc accattgatt acaccaatga tctactctac   10140
tgggcagatg cccacctggg ttacatagag tactctgatt tggagggcca ccatcgacac   10200
acggtgtatg atggggcact gcctcaccct ttcgctatta ccattttga agacactatt   10260 tattggacag attggaatac aaggacagtg gaaaagggaa acaaatatga tggatcaaat   10320
agacagacac tggtgaacac aacacacaga ccatttgaca tccatgtgta ccatccatat   10380
aggcagccca ttgtgagcaa tccctgtggt accaacaatg gtggctgttc tcatctctgc   10440
ctcatcaagc caggaggaaa agggttcact tgcgagtgtc cagatgactt ccgcaccctt   10500
caactgagtg gcagcaccta ctgcatgccc atgtgctcca gcacccagtt cctgtgcgct   10560
aacaatgaaa agtgcattcc tatctggtgg aaatgtgatg gacagaaaga ctgctcagat   10620
ggctctgatg aactggccct ttgcccgcag cgcttctgcc gactgggaca gttccagtgc   10680
agtgacggca actgcaccag cccgcagact ttatgcaatg ctcaccaaaa ttgccctgat   10740
gggtctgatg aagaccgtct tctttgtgag aatcaccact gtgactccaa tgaatggcag   10800
tgcgccaaca acgttgcat cccagaatcc tggcagtgtg acacatttaa cgactgtgag   10860
gataactcag atgaagacag ttcccactgt gccagcagga cctgccggcc gggccagttt   10920
cggtgtgcta atggccgctg catcccgcag gcctggaagt gtgatgtgga taatgattgt   10980
```

```
ggagaccact cggatgagcc cattgaagaa tgcatgagct ctgcccatct ctgtgacaac    11040
ttcacagaat tcagctgcaa acaaattac cgctgcatcc caaagtgggc cgtgtgcaat     11100
ggtgtagatg actgcaggga caacagtgat gagcaaggct gtgaggagag acatgccat     11160 cctgtggggg atttccgctg taaaaatcac cactgcatcc ctcttcgttg gcagtgtgat    11220
gggcaaaatg actgtggaga taactcagat gaggaaaact gtgctccccg ggagtgcaca    11280
gagagcgagt ttcgatgtgt caatcagcag tgcattccct cgcgatggat ctgtgaccat    11340
tacaacgact gtggggacaa ctcagatgaa cgggactgtg agatgaggac ctgccatcct    11400
gaatattttc agtgtacaag tggacattgt gtacacagtg aactgaaatg cgatggatcc    11460
gctgactgtt tggatgcgtc tgatgaagct gattgtccca cacgctttcc tgatggtgca    11520
tactgccagg ctactatgtt cgaatgcaaa aaccatgttt gtatcccgcc atattggaaa    11580
tgtgatggcg atgatgactg tggcgatggt tcagatgaag aacttcacct gtgcttggat    11640
gttccctgta attcaccaaa ccgttccgg tgtgacaaca atcgctgcat ttatagtcat     11700
gaggtgtgca atggtgtgga tgactgtgga gatggaactg atgagacaga ggagcactgt    11760
agaaaaccga cccctaaacc ttgtacagaa tatgaatata agtgtggcaa tgggcattgc    11820
attccacatg acaatgtgtg tgatgatgcc gatgactgtg gtgactggtc cgatgaactg    11880
ggttgcaata aggaaaaga aagaacatgt gctgaaaata tatgcgagca aaattgtacc    11940
caattaaatg aaggaggatt tatctgctcc tgtacagctg ggttcgaaac caatgttttt    12000
gacagaacct cctgtctaga tatcaatgaa tgtgaacaat ttgggacttg tccccagcac   12060
tgcagaaata ccaaaggaag ttatgagtgt gtctgtgctg atggcttcac gtctatgagt    12120
gaccgccctg gaaaacgatg tgcagctgag ggtagctctc ctttgttgct actgcctgac    12180
aatgtccgaa ttcgaaaata taatctctca tctgagaggt tctcagagta tcttcaagat    12240
gaggaatata tccaagctgt tgattatgat tgggatccca aggacatagg cctcagtgtt    12300
gtgtattaca ctgtgcgagg ggagggctct aggtttggtg ctatcaaacg tgcctacatc    12360
cccaactttg aatccggccg caataatctt gtgcaggaag ttgacctgaa actgaaatac    12420
gtaatgcagc cagatggaat agcagtggac tgggttggaa ggcatattta ctggtcagat    12480
gtcaagaata aacgcattga ggtggctaaa cttgatggaa ggtacagaaa gtggctgatt    12540
tccactgacc tggaccaacc agctgctatt gctgtgaatc ccaaactagg gcttatgttc    12600
tggactgact ggggaaagga acctaaaatc gagtctgcct ggatgaatgg agaggaccgc    12660
aacatcctgg ttttcgagga ccttggttgg ccaactggcc tttctatcga ttatttgaac    12720
aatgaccgaa tctactggag tgacttcaag gaggacgtta ttgaaaccat aaaatatgat    12780
gggactgata ggagagtcat tgcaaaggaa gcaatgaacc cttacagcct ggacatcttt    12840
gaagaccagt tatactggat atctaaggaa aaggagaag tatggaaaca aaataaattt    12900
gggcaaggaa agaaagagaa aacgctggta gtgaacccctt ggctcactca agttcgaatc    12960
tttcatcaac tcagatacaa taagtcagtg cccaacctttt gcaaacagat ctgcagccac   13020
ctctgccttc tgagacctgg aggatacagc tgtgcctgtc cccaaggctc cagctttata    13080
gaggggagca ccactgagtg tgatgcagcc atcgaactgc ctatcaacct gcccccccca   13140
tgcaggtgca tgcacggagg aaattgctat tttgatgaga ctgacctccc caaatgcaag    13200
tgtcctagcg gctacaccgg aaaatattgt gaaatggcgt tttcaaaagg catctctcca    13260
ggaacaaccg cagtagctgt gctgttgaca atcctcttga tcgtcgtaat tggagctctg    13320
gcaattgcag gattcttcca ctatagaagg accggctccc ttttgcctgc tctgcccaag    13380
```

-continued

```
ctgccaagct taagcagtct cgtcaagccc tctgaaaatg ggaatggggt gaccttcaga   13440
tcaggggcag atcttaacat ggatattgga gtgtctggtt ttggacctga gactgctatt   13500
gacaggtcaa tggcaatgag tgaagacttt gtcatggaaa tggggaagca gcccataata   13560
tttgaaaacc caatgtactc agccagagac agtgctgtca aagtggttca gccaatccag   13620
gtgactgtat ctgaaaatgt ggataataag aattatggaa gtcccataaa cccttctgag   13680
atagttccag agacaaaccc aacttcacca gctgctgatg gaactcaggt gacaaaatgg   13740
aatctcttca acgaaaatc taaacaaact accaactttg aaaatccaat ctatgcacag   13800
atggagaacg agcaaaagga aagtgttgct gcgacaccac ctccatcacc ttcgctccct   13860
gctaagccta agcctccttc gagaagagac ccaactccaa cctattctgc aacagaagac   13920
acttttaaag acaccgcaaa tcttgttaaa gaagactctg aagtatag              13968
```

<210> SEQ ID NO 2
<211> LENGTH: 4655
<212> TYPE: PRT
<213> ORGANISM: Homo sapiens

<400> SEQUENCE: 2

```
Met Asp Arg Gly Pro Ala Ala Val Ala Cys Thr Leu Leu Ala Leu
  1               5                  10                  15

Val Ala Cys Leu Ala Pro Ala Ser Gly Gln Glu Cys Asp Ser Ala His
                 20                  25                  30

Phe Arg Cys Gly Ser Gly His Cys Ile Pro Ala Asp Trp Arg Cys Asp
         35                  40                  45

Gly Thr Lys Asp Cys Ser Asp Asp Ala Asp Glu Ile Gly Cys Ala Val
     50                  55                  60

Val Thr Cys Gln Gln Gly Tyr Phe Lys Cys Gln Ser Glu Gly Gln Cys
 65                  70                  75                  80

Ile Pro Ser Ser Trp Val Cys Asp Gln Asp Gln Asp Cys Asp Asp Gly
                 85                  90                  95

Ser Asp Glu Arg Gln Asp Cys Ser Gln Ser Thr Cys Ser Ser His Gln
             100                 105                 110

Ile Thr Cys Ser Asn Gly Gln Cys Ile Pro Ser Glu Tyr Arg Cys Asp
         115                 120                 125

His Val Arg Asp Cys Pro Asp Gly Ala Asp Glu Asn Asp Cys Gln Tyr
     130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
        195                 200                 205

Gln Asp Gly Ser Asp Glu His Ala Cys Asn Tyr Pro Thr Cys Gly Gly
    210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
            260                 265                 270
```

-continued

```
Cys Pro Glu Ser Gly Arg Cys Ile Ser Ile Tyr Lys Val Cys Asp Gly
        275                 280                 285

Ile Leu Asp Cys Pro Gly Arg Glu Asp Glu Asn Asn Thr Ser Thr Gly
290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
                340                 345                 350

Gln Ile Trp Gly Ile Cys Asp Gln Lys Cys Glu Ser Arg Pro Gly Arg
        355                 360                 365

His Leu Cys His Cys Glu Glu Gly Tyr Ile Leu Glu Arg Gly Gln Tyr
370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
        420                 425                 430

Tyr His Leu Gln Arg Val Phe Trp Thr Asp Thr Val Gln Asn Lys Val
        435                 440                 445

Phe Ser Val Asp Ile Asn Gly Leu Asn Ile Gln Glu Val Leu Asn Val
450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
                500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
                580                 585                 590

Thr Val Val His Gly Gly Ser Leu Ile Pro His Pro Phe Gly Val Ser
        595                 600                 605

Leu Phe Glu Gly Gln Val Phe Phe Thr Asp Trp Thr Lys Met Ala Val
610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
                660                 665                 670

Val Cys Val Leu Ser His Arg Thr Asp Asn Asp Gly Leu Gly Phe Arg
        675                 680                 685

Cys Lys Cys Thr Phe Gly Phe Gln Leu Asp Thr Asp Glu Arg His Cys
        690                 695                 700
```

-continued

```
Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Val Gly Ile Asp Phe Ala Gln Asp
            740                 745                 750

Ser Thr Ile Phe Phe Ser Asp Met Ser Lys His Met Ile Phe Lys Gln
        755                 760                 765

Lys Ile Asp Gly Thr Gly Arg Glu Ile Leu Ala Ala Asn Arg Val Glu
    770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
                820                 825                 830

Val His Pro Phe Ala Gly Tyr Leu Phe Phe Thr Asp Trp Phe Arg Pro
                835                 840                 845

Ala Lys Ile Met Arg Ala Trp Ser Asp Gly Ser His Leu Leu Pro Val
    850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Leu Gly His Ile Glu Gln
                900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
        930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
        995                 1000                1005

Asn His Leu Thr Cys Glu Gly Asp Pro Thr Asn Glu Pro Pro Thr Glu
    1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
                1045                1050                1055

Glu Gln Leu Cys Gly Thr Leu Asn Asn Thr Cys Ser Ser Ser Ala Phe
            1060                1065                1070

Thr Cys Gly His Gly Glu Cys Ile Pro Ala His Trp Arg Cys Asp Lys
        1075                1080                1085

Arg Asn Asp Cys Val Asp Gly Ser Asp Glu His Asn Cys Pro Thr His
    1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
```

-continued

```
                1125                1130                1135
Gly Ser Asp Glu Lys Asn Cys Asn Ser Thr Glu Thr Cys Gln Pro Ser
            1140                1145                1150
Gln Phe Asn Cys Pro Asn His Arg Cys Ile Asp Leu Ser Phe Val Cys
            1155                1160                1165
Asp Gly Asp Lys Asp Cys Val Asp Gly Ser Asp Glu Val Gly Cys Val
    1170                1175                1180
Leu Asn Cys Thr Ala Ser Gln Phe Lys Cys Ala Ser Gly Asp Lys Cys
1185                1190                1195                1200
Ile Gly Val Thr Asn Arg Cys Asp Gly Val Phe Asp Cys Ser Asp Asn
                1205                1210                1215
Ser Asp Glu Ala Gly Cys Pro Thr Arg Pro Gly Met Cys His Ser
            1220                1225                1230
Asp Glu Phe Gln Cys Gln Glu Asp Gly Ile Cys Ile Pro Asn Phe Trp
            1235                1240                1245
Glu Cys Asp Gly His Pro Asp Cys Leu Tyr Gly Ser Asp Glu His Asn
        1250                1255                1260
Ala Cys Val Pro Lys Thr Cys Pro Ser Ser Tyr Phe His Cys Asp Asn
1265                1270                1275                1280
Gly Asn Cys Ile His Arg Ala Trp Leu Cys Asp Arg Asp Asn Asp Cys
                1285                1290                1295
Gly Asp Met Ser Asp Glu Lys Asp Cys Pro Thr Gln Pro Phe Arg Cys
            1300                1305                1310
Pro Ser Trp Gln Trp Gln Cys Leu Gly His Asn Ile Cys Val Asn Leu
        1315                1320                1325
Ser Val Val Cys Asp Gly Ile Phe Asp Cys Pro Asn Gly Thr Asp Glu
    1330                1335                1340
Ser Pro Leu Cys Asn Gly Asn Ser Cys Ser Asp Phe Asn Gly Gly Cys
1345                1350                1355                1360
Thr His Glu Cys Val Gln Glu Pro Phe Gly Ala Lys Cys Leu Cys Pro
                1365                1370                1375
Leu Gly Phe Leu Leu Ala Asn Asp Ser Lys Thr Cys Glu Asp Ile Asp
            1380                1385                1390
Glu Cys Asp Ile Leu Gly Ser Cys Ser Gln His Cys Tyr Asn Met Arg
            1395                1400                1405
Gly Ser Phe Arg Cys Ser Cys Asp Thr Gly Tyr Met Leu Glu Ser Asp
        1410                1415                1420
Gly Arg Thr Cys Lys Val Thr Ala Ser Glu Ser Leu Leu Leu Val
1425                1430                1435                1440
Ala Ser Gln Asn Lys Ile Ile Ala Asp Ser Val Thr Ser Gln Val His
                1445                1450                1455
Asn Ile Tyr Ser Leu Val Glu Asn Gly Ser Tyr Ile Val Ala Val Asp
            1460                1465                1470
Phe Asp Ser Ile Ser Gly Arg Ile Phe Trp Ser Asp Ala Thr Gln Gly
            1475                1480                1485
Lys Thr Trp Ser Ala Phe Gln Asn Gly Thr Asp Arg Arg Val Val Phe
    1490                1495                1500
Asp Ser Ser Ile Ile Leu Thr Glu Thr Ile Ala Ile Asp Trp Val Gly
1505                1510                1515                1520
Arg Asn Leu Tyr Trp Thr Asp Tyr Ala Leu Glu Thr Ile Glu Val Ser
                1525                1530                1535
Lys Ile Asp Gly Ser His Arg Thr Val Leu Ile Ser Lys Asn Leu Thr
            1540                1545                1550
```

-continued

Asn Pro Arg Gly Leu Ala Leu Asp Pro Arg Met Asn Glu His Leu Leu
    1555                1560                1565

Phe Trp Ser Asp Trp Gly His Pro Arg Ile Glu Arg Ala Ser Met
    1570                1575                1580

Asp Gly Ser Met Arg Thr Val Ile Val Gln Asp Lys Ile Phe Trp Pro
1585                1590                1595                1600

Cys Gly Leu Thr Ile Asp Tyr Pro Asn Arg Leu Leu Tyr Phe Met Asp
                1605                1610                1615

Ser Tyr Leu Asp Tyr Met Asp Phe Cys Asp Tyr Asn Gly His His Arg
    1620                1625                1630

Arg Gln Val Ile Ala Ser Asp Leu Ile Ile Arg His Pro Tyr Ala Leu
    1635                1640                1645

Thr Leu Phe Glu Asp Ser Val Tyr Trp Thr Asp Arg Ala Thr Arg Arg
    1650                1655                1660

Val Met Arg Ala Asn Lys Trp His Gly Gly Asn Gln Ser Val Val Met
1665                1670                1675                1680

Tyr Asn Ile Gln Trp Pro Leu Gly Ile Val Ala Val His Pro Ser Lys
                1685                1690                1695

Gln Pro Asn Ser Val Asn Pro Cys Ala Phe Ser Arg Cys Ser His Leu
    1700                1705                1710

Cys Leu Leu Ser Ser Gln Gly Pro His Phe Tyr Ser Cys Val Cys Pro
    1715                1720                1725

Ser Gly Trp Ser Leu Ser Pro Asp Leu Leu Asn Cys Leu Arg Asp Asp
    1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
                1765                1770                1775

Ile Gln Asn Gly Leu Asp Val Glu Phe Asp Asp Ala Glu Gln Tyr Ile
    1780                1785                1790

Tyr Trp Val Glu Asn Pro Gly Glu Ile His Arg Val Lys Thr Asp Gly
    1795                1800                1805

Thr Asn Arg Thr Val Phe Ala Ser Ile Ser Met Val Gly Pro Ser Met
    1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
                1845                1850                1855

Arg Lys Thr Leu Ile Ala Asn Asp Gly Thr Ala Leu Gly Val Gly Phe
    1860                1865                1870

Pro Ile Gly Ile Thr Val Asp Pro Ala Arg Gly Lys Leu Tyr Trp Ser
    1875                1880                1885

Asp Gln Gly Thr Asp Ser Gly Val Pro Ala Lys Ile Ala Ser Ala Asn
    1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Lys Leu Tyr Trp Ala
                1925                1930                1935

Val Thr Gly Arg Gly Val Ile Glu Arg Gly Asn Val Asp Gly Thr Asp
    1940                1945                1950

Arg Met Ile Leu Val His Gln Leu Ser His Pro Trp Gly Ile Ala Val
    1955                1960                1965

His Asp Ser Phe Leu Tyr Tyr Thr Asp Glu Gln Tyr Glu Val Ile Glu
    1970                1975                1980

```
Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Asn Ala Ala
        2005                2010                2015

Glu Ser Ser Asn Gly Cys Ser Asn Asn Met Asn Ala Cys Gln Gln Ile
            2020                2025                2030

Cys Leu Pro Val Pro Gly Gly Leu Phe Ser Cys Ala Cys Ala Thr Gly
        2035                2040                2045

Phe Lys Leu Asn Pro Asp Asn Arg Ser Cys Ser Pro Tyr Asn Ser Phe
    2050                2055                2060

Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
            2085                2090                2095

Ala Leu His Val Asp Val Asp Val Ser Ser Gly Phe Ile Tyr Trp Cys
        2100                2105                2110

Asp Phe Ser Ser Ser Val Ala Ser Asp Asn Ala Ile Arg Arg Ile Lys
    2115                2120                2125

Pro Asp Gly Ser Ser Leu Met Asn Ile Val Thr His Gly Ile Gly Glu
2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
        2165                2170                2175

Asn Thr Thr Tyr Arg Arg Val Leu Leu Lys Val Thr Val Asp Met Pro
        2180                2185                2190

Arg His Ile Val Val Asp Pro Lys Asn Arg Tyr Leu Phe Trp Ala Asp
    2195                2200                2205

Tyr Gly Gln Arg Pro Lys Ile Glu Arg Ser Phe Leu Asp Cys Thr Asn
    2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Ser Leu Asp
            2245                2250                2255

Ile Ile Ala Arg Ile Arg Ile Asn Gly Glu Asn Ser Glu Val Ile Arg
        2260                2265                2270

Tyr Gly Ser Arg Tyr Pro Thr Pro Tyr Gly Ile Thr Val Phe Glu Asn
    2275                2280                2285

Ser Ile Ile Trp Val Asp Arg Asn Leu Lys Lys Ile Phe Gln Ala Ser
2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
        2325                2330                2335

Ser Pro Ala Glu Val Asn Asn Asn Pro Cys Leu Glu Asn Asn Gly Gly
        2340                2345                2350

Cys Ser His Leu Cys Phe Ala Leu Pro Gly Leu His Thr Pro Lys Cys
        2355                2360                2365

Asp Cys Ala Phe Gly Thr Leu Gln Ser Asp Gly Lys Asn Cys Ala Ile
    2370                2375                2380

Ser Thr Glu Asn Phe Leu Ile Phe Ala Leu Ser Asn Ser Leu Arg Ser
2385                2390                2395                2400

Leu His Leu Asp Pro Glu Asn His Ser Pro Pro Phe Gln Thr Ile Asn
```

-continued

```
                2405                2410                2415
Val Glu Arg Thr Val Met Ser Leu Asp Tyr Asp Ser Val Ser Asp Arg
            2420                2425                2430
Ile Tyr Phe Thr Gln Asn Leu Ala Ser Gly Val Gly Gln Ile Ser Tyr
            2435                2440                2445
Ala Thr Leu Ser Ser Gly Ile His Thr Pro Thr Val Ile Ala Ser Gly
            2450                2455                2460
Ile Gly Thr Ala Asp Gly Ile Ala Phe Asp Trp Ile Thr Arg Arg Ile
2465                2470                2475                2480
Tyr Tyr Ser Asp Tyr Leu Asn Gln Met Ile Asn Ser Met Ala Glu Asp
                2485                2490                2495
Gly Ser Asn Arg Thr Val Ile Ala Arg Val Pro Lys Pro Arg Ala Ile
            2500                2505                2510
Val Leu Asp Pro Cys Gln Gly Tyr Leu Tyr Trp Ala Asp Trp Asp Thr
            2515                2520                2525
His Ala Lys Ile Glu Arg Ala Thr Leu Gly Gly Asn Phe Arg Val Pro
            2530                2535                2540
Ile Val Asn Ser Ser Leu Val Met Pro Ser Gly Leu Thr Leu Asp Tyr
2545                2550                2555                2560
Glu Glu Asp Leu Leu Tyr Trp Val Asp Ala Ser Leu Gln Arg Ile Glu
                2565                2570                2575
Arg Ser Thr Leu Thr Gly Val Asp Arg Glu Val Ile Val Asn Ala Ala
            2580                2585                2590
Val His Ala Phe Gly Leu Thr Leu Tyr Gly Gln Tyr Ile Tyr Trp Thr
            2595                2600                2605
Asp Leu Tyr Thr Gln Arg Ile Tyr Arg Ala Asn Lys Tyr Asp Gly Ser
            2610                2615                2620
Gly Gln Ile Ala Met Thr Thr Asn Leu Leu Ser Gln Pro Arg Gly Ile
2625                2630                2635                2640
Asn Thr Val Val Lys Asn Gln Lys Gln Gln Cys Asn Asn Pro Cys Glu
                2645                2650                2655
Gln Phe Asn Gly Gly Cys Ser His Ile Cys Ala Pro Gly Pro Asn Gly
            2660                2665                2670
Ala Glu Cys Gln Cys Pro His Glu Gly Asn Trp Tyr Leu Ala Asn Asn
            2675                2680                2685
Arg Lys His Cys Ile Val Asp Asn Gly Glu Arg Cys Gly Ala Ser Ser
            2690                2695                2700
Phe Thr Cys Ser Asn Gly Arg Cys Ile Ser Glu Glu Trp Lys Cys Asp
2705                2710                2715                2720
Asn Asp Asn Asp Cys Gly Asp Gly Ser Asp Glu Met Glu Ser Val Cys
                2725                2730                2735
Ala Leu His Thr Cys Ser Pro Thr Ala Phe Thr Cys Ala Asn Gly Arg
            2740                2745                2750
Cys Val Gln Tyr Ser Tyr Arg Cys Asp Tyr Tyr Asn Asp Cys Gly Asp
            2755                2760                2765
Gly Ser Asp Glu Ala Gly Cys Leu Phe Arg Asp Cys Asn Ala Thr Thr
            2770                2775                2780
Glu Phe Met Cys Asn Asn Arg Arg Cys Ile Pro Arg Glu Phe Ile Cys
2785                2790                2795                2800
Asn Gly Val Asp Asn Cys His Asp Asn Asn Thr Ser Asp Glu Lys Asn
                2805                2810                2815
Cys Pro Asp Arg Thr Cys Gln Ser Gly Tyr Thr Lys Cys His Asn Ser
            2820                2825                2830
```

```
Asn Ile Cys Ile Pro Arg Val Tyr Leu Cys Asp Gly Asp Asn Asp Cys
         2835                2840                2845

Gly Asp Asn Ser Asp Glu Asn Pro Thr Tyr Cys Thr His Thr Cys
    2850                2855                2860

Ser Ser Ser Glu Phe Gln Cys Ala Ser Gly Arg Cys Ile Pro Gln His
2865            2870                2875                2880

Trp Tyr Cys Asp Gln Glu Thr Asp Cys Phe Asp Ala Ser Asp Glu Pro
            2885                2890                2895

Ala Ser Cys Gly His Ser Glu Arg Thr Cys Leu Ala Asp Glu Phe Lys
        2900                2905                2910

Cys Asp Gly Gly Arg Cys Ile Pro Ser Glu Trp Ile Cys Asp Gly Asp
        2915                2920                2925

Asn Asp Cys Gly Asp Met Ser Asp Glu Asp Lys Arg His Gln Cys Gln
    2930                2935                2940

Asn Gln Asn Cys Ser Asp Ser Glu Phe Leu Cys Val Asn Asp Arg Pro
2945            2950                2955                2960

Pro Asp Arg Arg Cys Ile Pro Gln Ser Trp Val Cys Asp Gly Asp Val
            2965                2970                2975

Asp Cys Thr Asp Gly Tyr Asp Glu Asn Gln Asn Cys Thr Arg Arg Thr
        2980                2985                2990

Cys Ser Glu Asn Glu Phe Thr Cys Gly Tyr Gly Leu Cys Ile Pro Lys
    2995                3000                3005

Ile Phe Arg Cys Asp Arg His Asn Asp Cys Gly Asp Tyr Ser Asp Glu
        3010                3015                3020

Arg Gly Cys Leu Tyr Gln Thr Cys Gln Gln Asn Gln Phe Thr Cys Gln
3025            3030                3035                3040

Asn Gly Arg Cys Ile Ser Lys Thr Phe Val Cys Asp Glu Asp Asn Asp
            3045                3050                3055

Cys Gly Asp Gly Ser Asp Glu Leu Met His Leu Cys His Thr Pro Glu
    3060                3065                3070

Pro Thr Cys Pro Pro His Glu Phe Lys Cys Asp Asn Gly Arg Cys Ile
        3075                3080                3085

Glu Met Met Lys Leu Cys Asn His Leu Asp Asp Cys Leu Asp Asn Ser
    3090                3095                3100

Asp Glu Lys Gly Cys Gly Ile Asn Glu Cys His Asp Pro Ser Ile Ser
3105            3110                3115                3120

Gly Cys Asp His Asn Cys Thr Asp Thr Leu Thr Ser Phe Tyr Cys Ser
            3125                3130                3135

Cys Arg Pro Gly Tyr Lys Leu Met Ser Asp Lys Arg Thr Cys Val Asp
        3140                3145                3150

Ile Asp Glu Cys Thr Glu Met Pro Phe Val Cys Ser Gln Lys Cys Glu
    3155                3160                3165

Asn Val Ile Gly Ser Tyr Ile Cys Lys Cys Ala Pro Gly Tyr Leu Arg
3170            3175                3180

Glu Pro Asp Gly Lys Thr Cys Arg Gln Asn Ser Asn Ile Glu Pro Tyr
    3185                3190                3195                3200

Leu Ile Phe Ser Asn Arg Tyr Tyr Leu Arg Asn Leu Thr Ile Asp Gly
            3205                3210                3215

Tyr Phe Tyr Ser Leu Ile Leu Glu Gly Leu Asp Asn Val Val Ala Leu
        3220                3225                3230

Asp Phe Asp Arg Val Glu Lys Arg Leu Tyr Trp Ile Asp Thr Gln Arg
        3235                3240                3245

Gln Val Ile Glu Arg Met Phe Leu Asn Lys Thr Asn Lys Glu Thr Ile
    3250                3255                3260
```

-continued

```
Ile Asn His Arg Leu Pro Ala Ala Glu Ser Leu Ala Val Asp Trp Val
3265                3270                3275                3280

Ser Arg Lys Leu Tyr Trp Leu Asp Ala Arg Leu Asp Gly Leu Phe Val
            3285                3290                3295

Ser Asp Leu Asn Gly Gly His Arg Arg Met Leu Ala Gln His Cys Val
        3300                3305                3310

Asp Ala Asn Asn Thr Phe Cys Phe Asp Asn Pro Arg Gly Leu Ala Leu
    3315                3320                3325

His Pro Gln Tyr Gly Tyr Leu Tyr Trp Ala Asp Trp Gly His Arg Ala
3330                3335                3340

Tyr Ile Gly Arg Val Gly Met Asp Gly Thr Asn Lys Ser Val Ile Ile
3345                3350                3355                3360

Ser Thr Lys Leu Glu Trp Pro Asn Gly Ile Thr Ile Asp Tyr Thr Asn
            3365                3370                3375

Asp Leu Leu Tyr Trp Ala Asp Ala His Leu Gly Tyr Ile Glu Tyr Ser
        3380                3385                3390

Asp Leu Glu Gly His His Arg His Thr Val Tyr Asp Gly Ala Leu Pro
    3395                3400                3405

His Pro Phe Ala Ile Thr Ile Phe Glu Asp Thr Ile Tyr Trp Thr Asp
3410                3415                3420

Trp Asn Thr Arg Thr Val Glu Lys Gly Asn Lys Tyr Asp Gly Ser Asn
3425                3430                3435                3440

Arg Gln Thr Leu Val Asn Thr Thr His Arg Pro Phe Asp Ile His Val
            3445                3450                3455

Tyr His Pro Tyr Arg Gln Pro Ile Val Ser Asn Pro Cys Gly Thr Asn
        3460                3465                3470

Asn Gly Gly Cys Ser His Leu Cys Leu Ile Lys Pro Gly Gly Lys Gly
    3475                3480                3485

Phe Thr Cys Glu Cys Pro Asp Asp Phe Arg Thr Leu Gln Leu Ser Gly
    3490                3495                3500

Ser Thr Tyr Cys Met Pro Met Cys Ser Ser Thr Gln Phe Leu Cys Ala
3505                3510                3515                3520

Asn Asn Glu Lys Cys Ile Pro Ile Trp Trp Lys Cys Asp Gly Gln Lys
            3525                3530                3535

Asp Cys Ser Asp Gly Ser Asp Glu Leu Ala Leu Cys Pro Gln Arg Phe
        3540                3545                3550

Cys Arg Leu Gly Gln Phe Gln Cys Ser Asp Gly Asn Cys Thr Ser Pro
    3555                3560                3565

Gln Thr Leu Cys Asn Ala His Gln Asn Cys Pro Asp Gly Ser Asp Glu
    3570                3575                3580

Asp Arg Leu Leu Cys Glu Asn His His Cys Asp Ser Asn Glu Trp Gln
3585                3590                3595                3600

Cys Ala Asn Lys Arg Cys Ile Pro Glu Ser Trp Gln Cys Asp Thr Phe
            3605                3610                3615

Asn Asp Cys Glu Asp Asn Ser Asp Glu Asp Ser Ser His Cys Ala Ser
        3620                3625                3630

Arg Thr Cys Arg Pro Gly Gln Phe Arg Cys Ala Asn Gly Arg Cys Ile
    3635                3640                3645

Pro Gln Ala Trp Lys Cys Asp Val Asp Asn Asp Cys Gly Asp His Ser
    3650                3655                3660

Asp Glu Pro Ile Glu Glu Cys Met Ser Ala His Leu Cys Asp Asn
3665                3670                3675                3680

Phe Thr Glu Phe Ser Cys Lys Thr Asn Tyr Arg Cys Ile Pro Lys Trp
```

-continued

```
                    3685                3690                3695
Ala Val Cys Asn Gly Val Asp Asp Cys Arg Asp Asn Ser Asp Glu Gln
            3700                3705                3710
Gly Cys Glu Glu Arg Thr Cys His Pro Val Gly Asp Phe Arg Cys Lys
            3715                3720                3725
Asn His His Cys Ile Pro Leu Arg Trp Gln Cys Asp Gly Gln Asn Asp
            3730                3735                3740
Cys Gly Asp Asn Ser Asp Glu Glu Asn Cys Ala Pro Arg Glu Cys Thr
3745                3750                3755                3760
Glu Ser Glu Phe Arg Cys Val Asn Gln Gln Cys Ile Pro Ser Arg Trp
            3765                3770                3775
Ile Cys Asp His Tyr Asn Asp Cys Gly Asp Asn Ser Asp Glu Arg Asp
            3780                3785                3790
Cys Glu Met Arg Thr Cys His Pro Glu Tyr Phe Gln Cys Thr Ser Gly
            3795                3800                3805
His Cys Val His Ser Glu Leu Lys Cys Asp Gly Ser Ala Asp Cys Leu
            3810                3815                3820
Asp Ala Ser Asp Glu Ala Asp Cys Pro Thr Arg Phe Pro Asp Gly Ala
3825                3830                3835                3840
Tyr Cys Gln Ala Thr Met Phe Glu Cys Lys Asn His Val Cys Ile Pro
            3845                3850                3855
Pro Tyr Trp Lys Cys Asp Gly Asp Asp Cys Gly Asp Gly Ser Asp
            3860                3865                3870
Glu Glu Leu His Leu Cys Leu Asp Val Pro Cys Asn Ser Pro Asn Arg
            3875                3880                3885
Phe Arg Cys Asp Asn Asn Arg Cys Ile Tyr Ser His Glu Val Cys Asn
            3890                3895                3900
Gly Val Asp Asp Cys Gly Asp Gly Thr Asp Glu Thr Glu Glu His Cys
3905                3910                3915                3920
Arg Lys Pro Thr Pro Lys Pro Cys Thr Glu Tyr Glu Tyr Lys Cys Gly
            3925                3930                3935
Asn Gly His Cys Ile Pro His Asp Asn Val Cys Asp Asp Ala Asp Asp
            3940                3945                3950
Cys Gly Asp Trp Ser Asp Glu Leu Gly Cys Asn Lys Gly Lys Glu Arg
            3955                3960                3965
Thr Cys Ala Glu Asn Ile Cys Glu Gln Asn Cys Thr Gln Leu Asn Glu
            3970                3975                3980
Gly Gly Phe Ile Cys Ser Cys Thr Ala Gly Phe Glu Thr Asn Val Phe
3985                3990                3995                4000
Asp Arg Thr Ser Cys Leu Asp Ile Asn Glu Cys Glu Gln Phe Gly Thr
            4005                4010                4015
Cys Pro Gln His Cys Arg Asn Thr Lys Gly Ser Tyr Glu Cys Val Cys
            4020                4025                4030
Ala Asp Gly Phe Thr Ser Met Ser Asp Arg Pro Gly Lys Arg Cys Ala
            4035                4040                4045
Ala Glu Gly Ser Ser Pro Leu Leu Leu Leu Pro Asp Asn Val Arg Ile
            4050                4055                4060
Arg Lys Tyr Asn Leu Ser Ser Glu Arg Phe Ser Glu Tyr Leu Gln Asp
4065                4070                4075                4080
Glu Glu Tyr Ile Gln Ala Val Asp Tyr Asp Trp Asp Pro Lys Asp Ile
            4085                4090                4095
Gly Leu Ser Val Val Tyr Tyr Thr Val Arg Gly Glu Gly Ser Arg Phe
            4100                4105                4110
```

-continued

```
Gly Ala Ile Lys Arg Ala Tyr Ile Pro Asn Phe Glu Ser Gly Arg Asn
            4115                4120                4125

Asn Leu Val Gln Glu Val Asp Leu Lys Leu Lys Tyr Val Met Gln Pro
        4130                4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
            4165                4170                4175

Lys Trp Leu Ile Ser Thr Asp Leu Asp Gln Pro Ala Ile Ala Val
        4180                4185                4190

Asn Pro Lys Leu Gly Leu Met Phe Trp Thr Asp Trp Gly Lys Glu Pro
        4195                4200                4205

Lys Ile Glu Ser Ala Trp Met Asn Gly Glu Asp Arg Asn Ile Leu Val
        4210                4215                4220

Phe Glu Asp Leu Gly Trp Pro Thr Gly Leu Ser Ile Asp Tyr Leu Asn
4225                4230                4235                4240

Asn Asp Arg Ile Tyr Trp Ser Asp Phe Lys Glu Asp Val Ile Glu Thr
            4245                4250                4255

Ile Lys Tyr Asp Gly Thr Asp Arg Arg Val Ile Ala Lys Glu Ala Met
        4260                4265                4270

Asn Pro Tyr Ser Leu Asp Ile Phe Glu Asp Gln Leu Tyr Trp Ile Ser
        4275                4280                4285

Lys Glu Lys Gly Glu Val Trp Lys Gln Asn Lys Phe Gly Gln Gly Lys
        4290                4295                4300

Lys Glu Lys Thr Leu Val Val Asn Pro Trp Leu Thr Gln Val Arg Ile
        4305                4310                4315                4320

Phe His Gln Leu Arg Tyr Asn Lys Ser Val Pro Asn Leu Cys Lys Gln
        4325                4330                4335

Ile Cys Ser His Leu Cys Leu Leu Arg Pro Gly Gly Tyr Ser Cys Ala
            4340                4345                4350

Cys Pro Gln Gly Ser Ser Phe Ile Glu Gly Ser Thr Thr Glu Cys Asp
        4355                4360                4365

Ala Ala Ile Glu Leu Pro Ile Asn Leu Pro Pro Pro Cys Arg Cys Met
        4370                4375                4380

His Gly Gly Asn Cys Tyr Phe Asp Glu Thr Asp Leu Pro Lys Cys Lys
4385                4390                4395                4400

Cys Pro Ser Gly Tyr Thr Gly Lys Tyr Cys Glu Met Ala Phe Ser Lys
            4405                4410                4415

Gly Ile Ser Pro Gly Thr Thr Ala Val Ala Val Leu Leu Thr Ile Leu
        4420                4425                4430

Leu Ile Val Val Ile Gly Ala Leu Ala Ile Ala Gly Phe Phe His Tyr
        4435                4440                4445

Arg Arg Thr Gly Ser Leu Leu Pro Ala Leu Pro Lys Leu Pro Ser Leu
        4450                4455                4460

Ser Ser Leu Val Lys Pro Ser Glu Asn Gly Asn Gly Val Thr Phe Arg
4465                4470                4475                4480

Ser Gly Ala Asp Leu Asn Met Asp Ile Gly Val Ser Gly Phe Gly Pro
            4485                4490                4495

Glu Thr Ala Ile Asp Arg Ser Met Ala Met Ser Glu Asp Phe Val Met
        4500                4505                4510

Glu Met Gly Lys Gln Pro Ile Ile Phe Glu Asn Pro Met Tyr Ser Ala
        4515                4520                4525

Arg Asp Ser Ala Val Lys Val Val Gln Pro Ile Gln Val Thr Val Ser
        4530                4535                4540
```

```
Glu Asn Val Asp Asn Lys Asn Tyr Gly Ser Pro Ile Asn Pro Ser Glu
4545                4550                4555                4560

Ile Val Pro Glu Thr Asn Pro Thr Ser Pro Ala Ala Asp Gly Thr Gln
                4565                4570                4575

Val Thr Lys Trp Asn Leu Phe Lys Arg Lys Ser Lys Gln Thr Thr Asn
            4580                4585                4590

Phe Glu Asn Pro Ile Tyr Ala Gln Met Glu Asn Glu Gln Lys Glu Ser
        4595                4600                4605

Val Ala Ala Thr Pro Pro Pro Ser Pro Ser Leu Pro Ala Lys Pro Lys
    4610                4615                4620

Pro Pro Ser Arg Arg Asp Pro Thr Pro Thr Tyr Ser Ala Thr Glu Asp
4625                4630                4635                4640

Thr Phe Lys Asp Thr Ala Asn Leu Val Lys Glu Asp Ser Glu Val
                4645                4650                4655
```